US006790674B2

(12) United States Patent
Wright et al.

(10) Patent No.: US 6,790,674 B2
(45) Date of Patent: Sep. 14, 2004

(54) SAMPLER

(75) Inventors: Paul George Wright, Binfield (GB); Lowell Robert Nickolaus, Lincoln, NE (US); Paul Thees Busboom, Pickrell, NE (US); Jerome John Kazakevicius, Omaha, NE (US); John D. Hull, Lincoln, NE (US); Ralph E. Setter, Edmond, OK (US); Larry Lee Fritz, Lincoln, NE (US); Frederick Detlef Sueverkruepp, III, Lincoln, NE (US); Jack William Foley, Seward, NE (US)

(73) Assignee: Isco, Inc., Lincoln, NE (US)

( * ) Notice: Subject to any disclaimer, the term of this patent is extended or adjusted under 35 U.S.C. 154(b) by 395 days.

(21) Appl. No.: 09/882,566

(22) Filed: Jun. 15, 2001

(65) Prior Publication Data

US 2002/0025255 A1 Feb. 28, 2002

Related U.S. Application Data

(60) Continuation-in-part of application No. 09/570,900, filed on May 15, 2000, now Pat. No. 6,494,331, which is a division of application No. 08/040,117, filed on Mar. 30, 1993, now Pat. No. 6,152,189.

(51) Int. Cl.[7] ................................................ B65B 3/00
(52) U.S. Cl. ..................... 436/180; 422/100; 141/2; 141/130; 141/260; 141/18; 73/864.24; 73/864.34
(58) Field of Search ................ 73/864.34, 864.24, 73/863.34; 422/100; 436/180, 54; 141/2, 130, 260, 18

(56) References Cited

U.S. PATENT DOCUMENTS

| | | | |
|---|---|---|---|
| 2,665,585 A | | 1/1954 | Marcell et al. |
| 3,093,165 A | * | 6/1963 | Risser ........................ 141/140 |
| 3,105,527 A | * | 10/1963 | Mayeux ...................... 141/275 |
| 3,589,410 A | * | 6/1971 | Manas ......................... 141/45 |
| 3,603,471 A | * | 9/1971 | Harris et al. ................ 215/247 |
| 3,757,981 A | * | 9/1973 | Harris et al. ................ 215/247 |
| 3,896,673 A | * | 7/1975 | Audouze et al. ......... 73/863.33 |
| 4,257,751 A | * | 3/1981 | Kofahl ....................... 417/394 |
| 4,517,851 A | * | 5/1985 | Tice ........................ 73/864.91 |
| 4,525,979 A | * | 7/1985 | Lin et al. ...................... 53/268 |
| 4,674,343 A | * | 6/1987 | Larson ..................... 73/864.35 |
| 4,705,667 A | * | 11/1987 | Marsoner et al. .......... 422/68.1 |
| 4,810,172 A | * | 3/1989 | Fiedler et al. .............. 417/394 |

(List continued on next page.)

FOREIGN PATENT DOCUMENTS

| | | |
|---|---|---|
| DE | 2 354 820 | 11/1973 |
| FR | 2 341 854 | 9/1977 |
| FR | 2 485 732 | 6/1980 |

OTHER PUBLICATIONS

Model AVOCS–500 Automatic Volatile Organic Composite Sampler, Associated Design and Manufacturing Company; Letter dated Nov. 14, 1992 explaining product catalog item.

New VOC Sampler, Model CKW, Edmund Buhler, GmbH & Company, P.O. Box 1021, Malibu, CA 90265; Dec. 16, 1991.

*Primary Examiner*—Jeffrey R. Snay
(74) *Attorney, Agent, or Firm*—Vincent L. Carney

(57) ABSTRACT

To sample hot liquids containing volatile materials, the liquid is cooled in a refrigerator and pumped through a syringe needle into a container until the container overflows. The needle is removed slowly and the container is automatically closed as the needle is withdrawn, wherein liquid flows upwardly continuously as the needle is withdrawn through an opening. The cap for the container includes a closure having a valve opening extending upwardly and sized to narrowly receive the syringe needle in a perpendicular valve member opening. The valve member includes a flat member on one end adapted to be gripped by a cam follower for opening and closing of the valve opening in coordination with the movement of the syringe needle.

60 Claims, 16 Drawing Sheets

U.S. PATENT DOCUMENTS

| | | | | |
|---|---|---|---|---|
| 4,862,932 A | * | 9/1989 | Feinstein et al. | 141/130 |
| 5,115,841 A | * | 5/1992 | Horino et al. | 141/250 |
| 5,147,185 A | * | 9/1992 | Niehaus et al. | 417/394 |
| 5,169,602 A | * | 12/1992 | Pang et al. | 422/103 |
| 5,173,265 A | * | 12/1992 | Golias et al. | 422/99 |
| 5,194,226 A | * | 3/1993 | Tomoff et al. | 422/100 |
| 5,217,053 A | * | 6/1993 | Foster et al. | 141/98 |
| 5,256,573 A | * | 10/1993 | Kuroda et al. | 436/179 |
| 5,279,167 A | * | 1/1994 | Peterson | 73/863.86 |

* cited by examiner

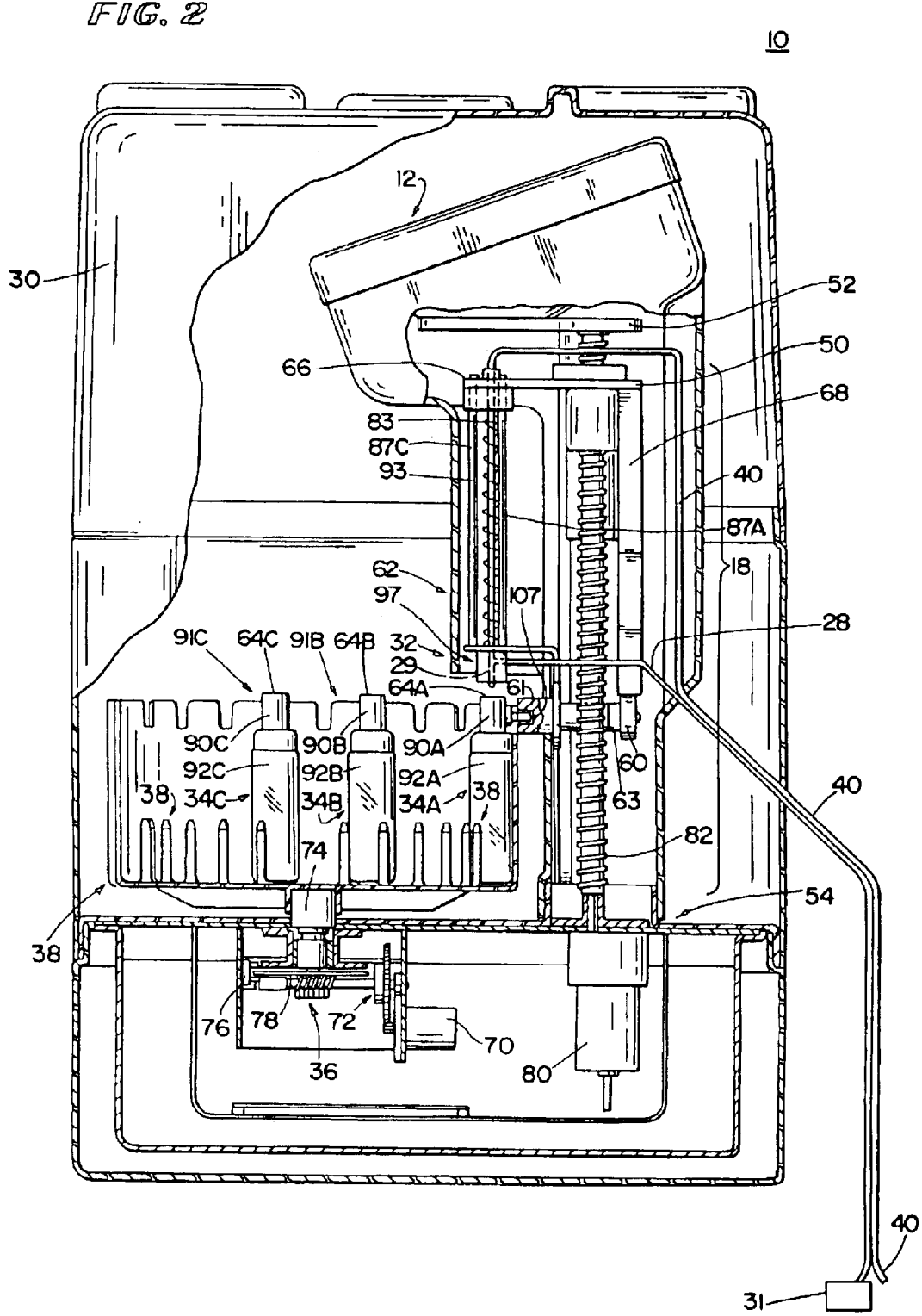

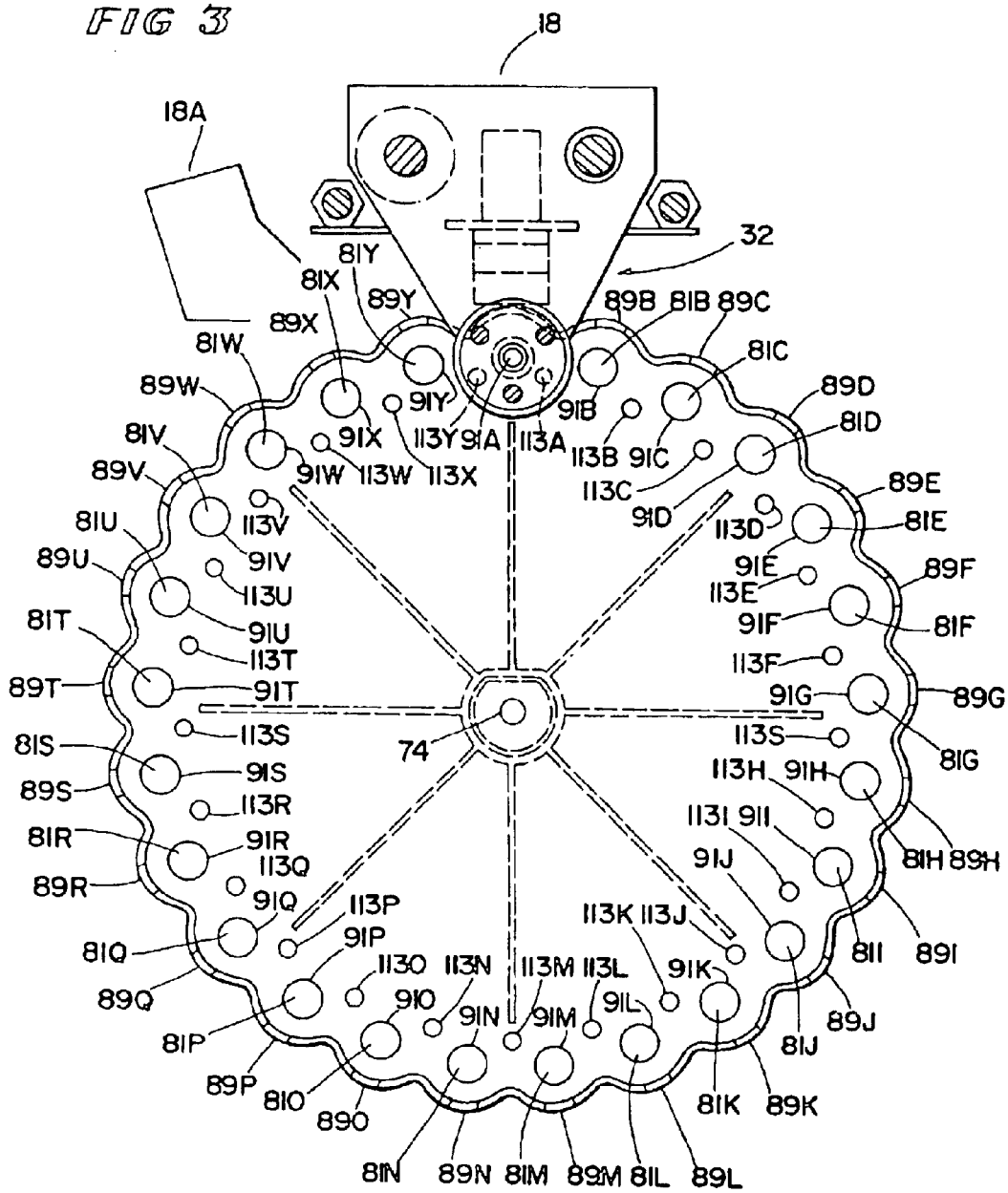

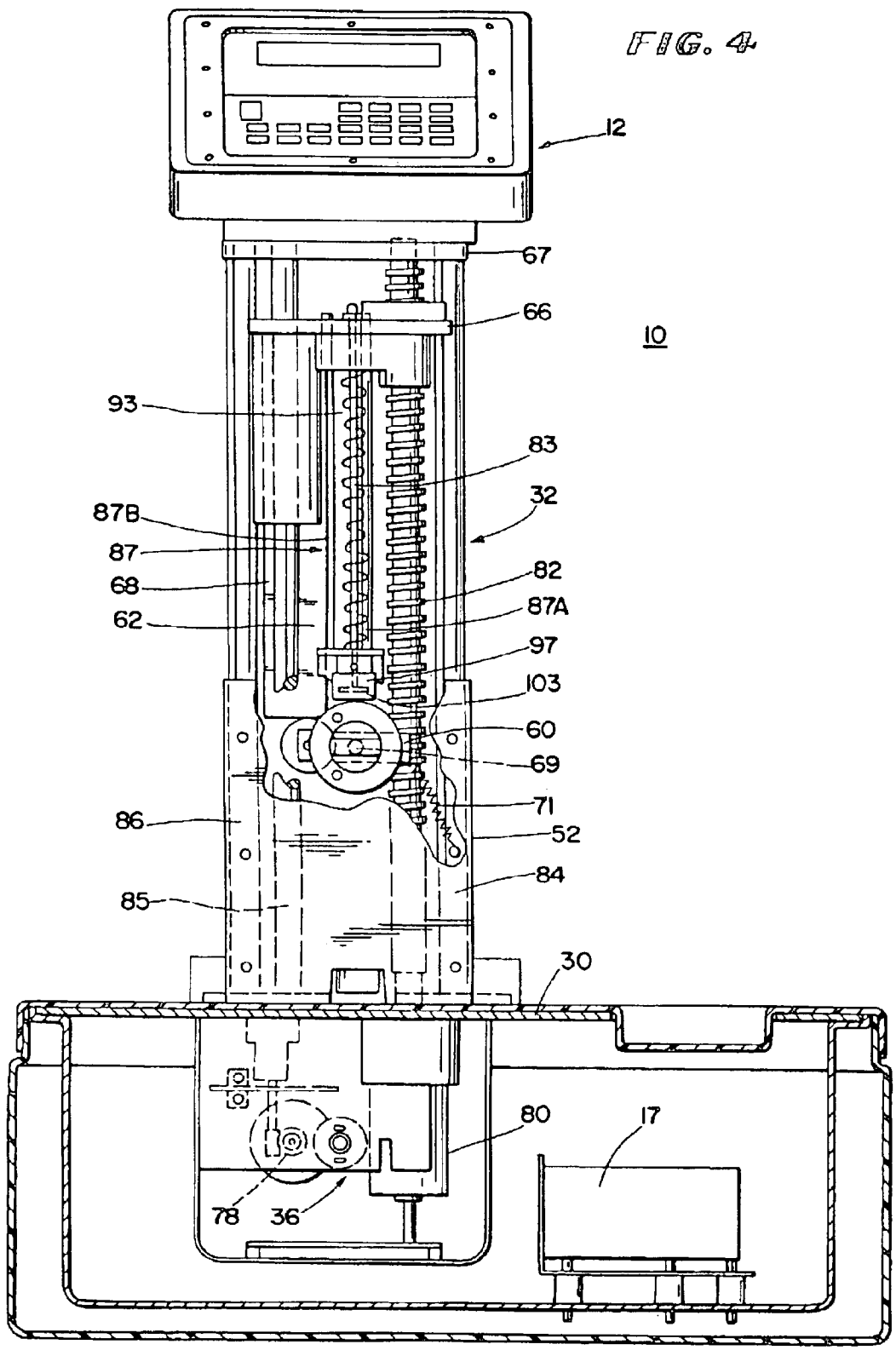

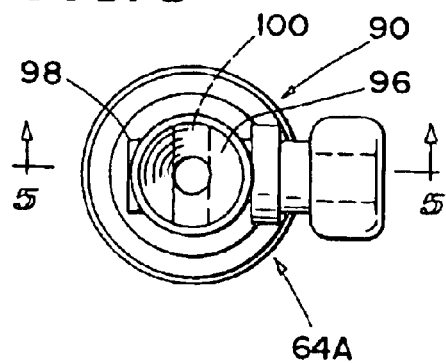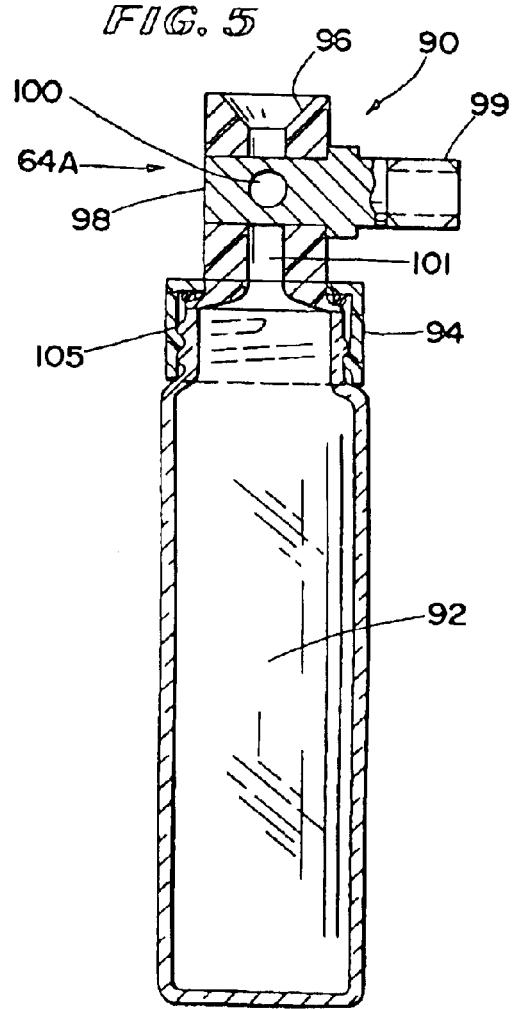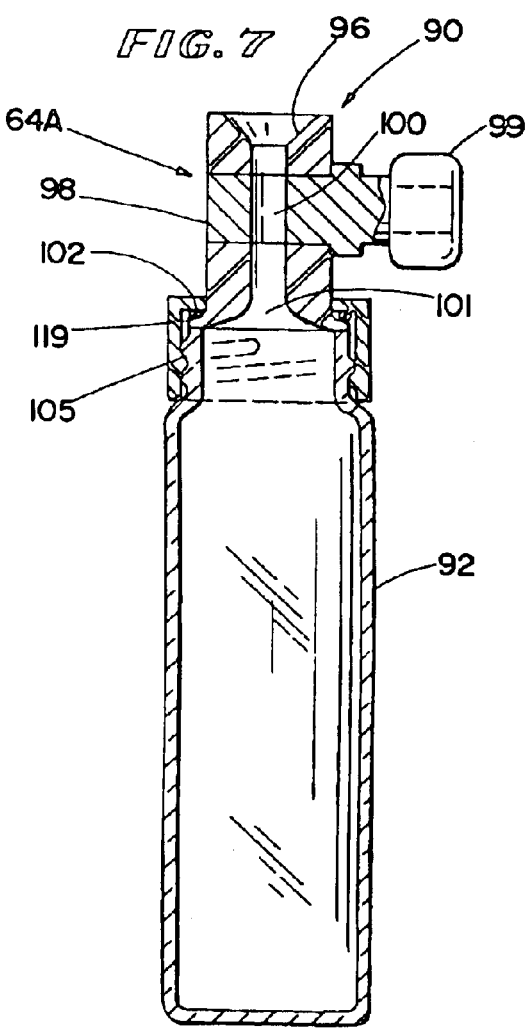

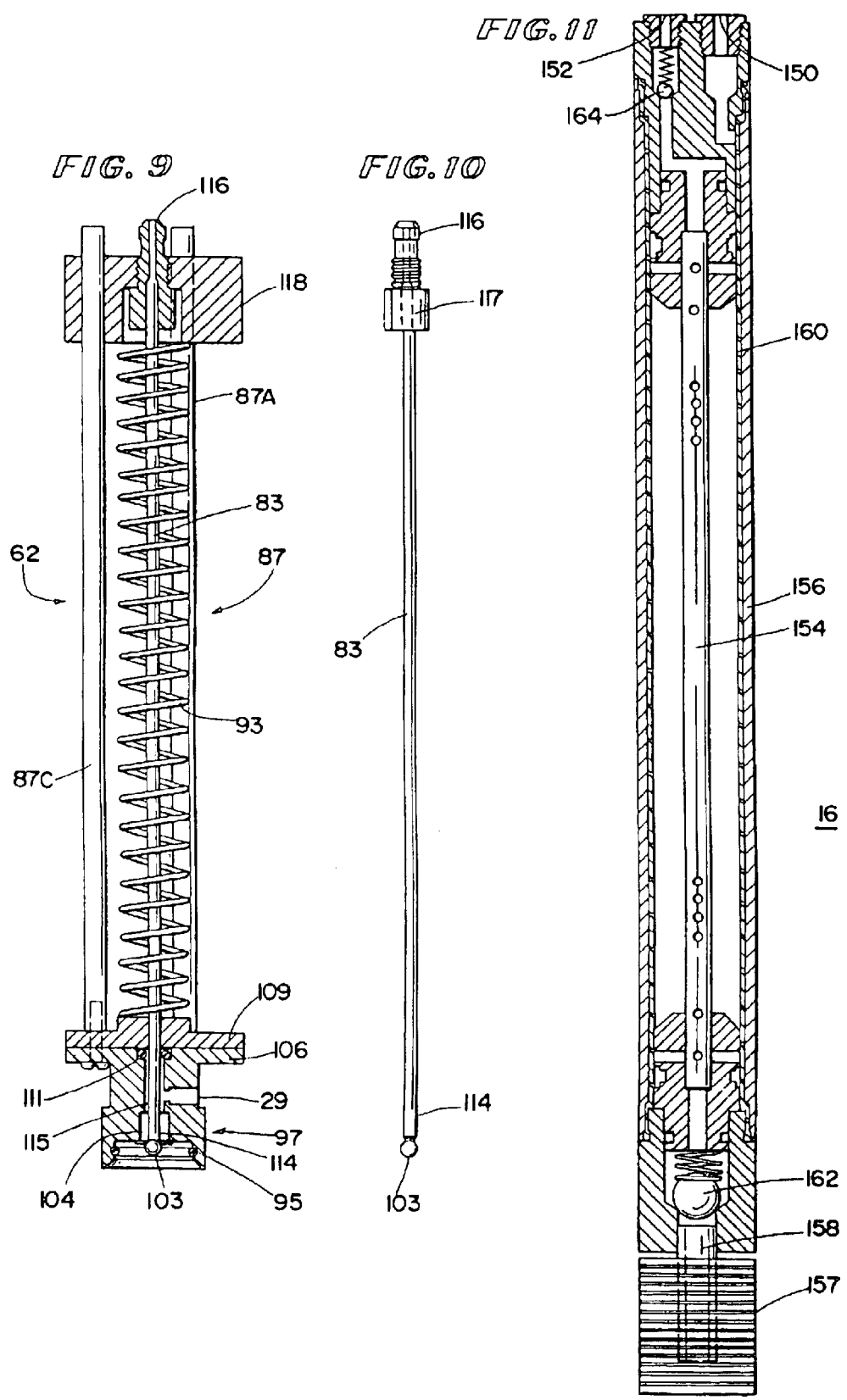

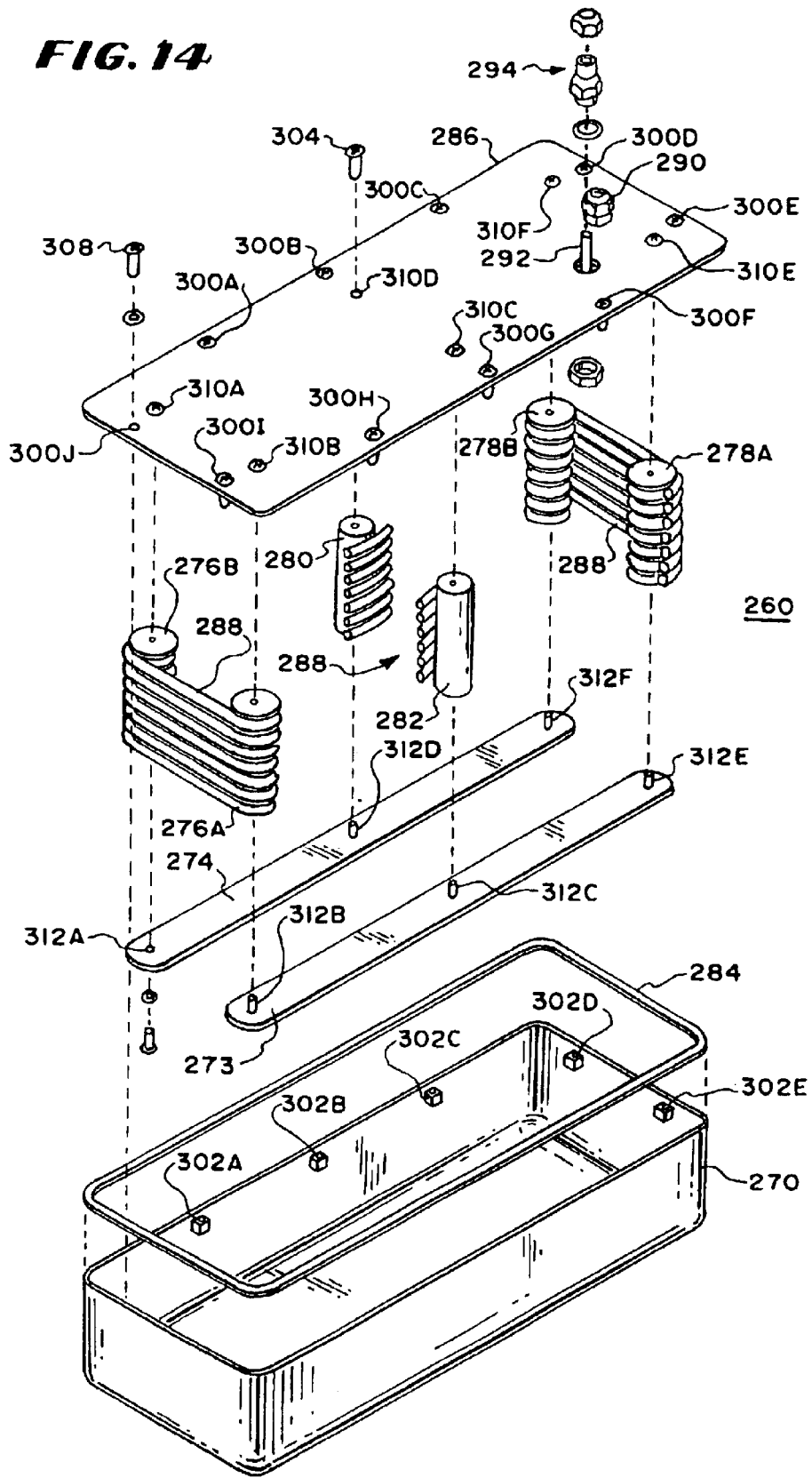

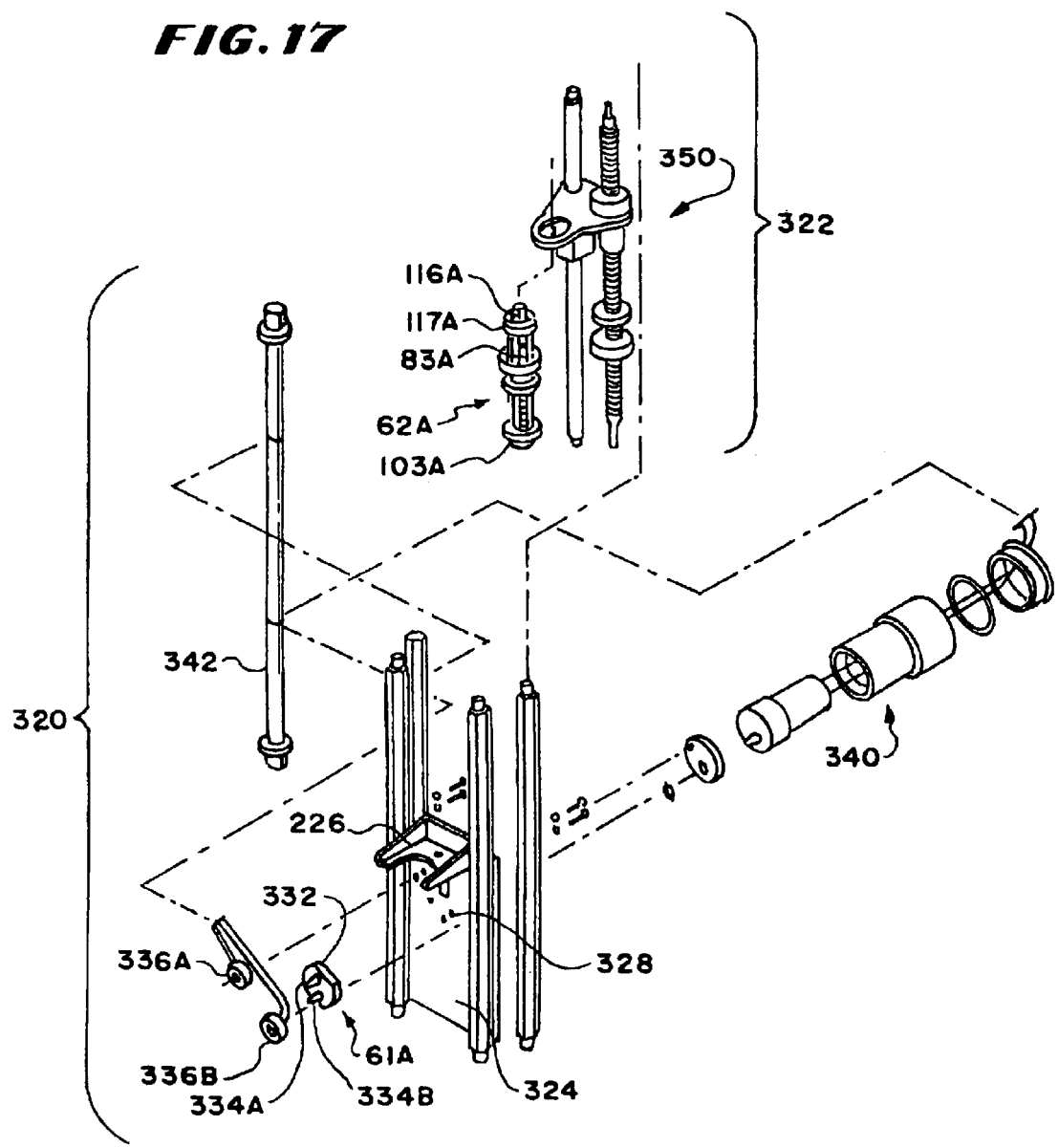

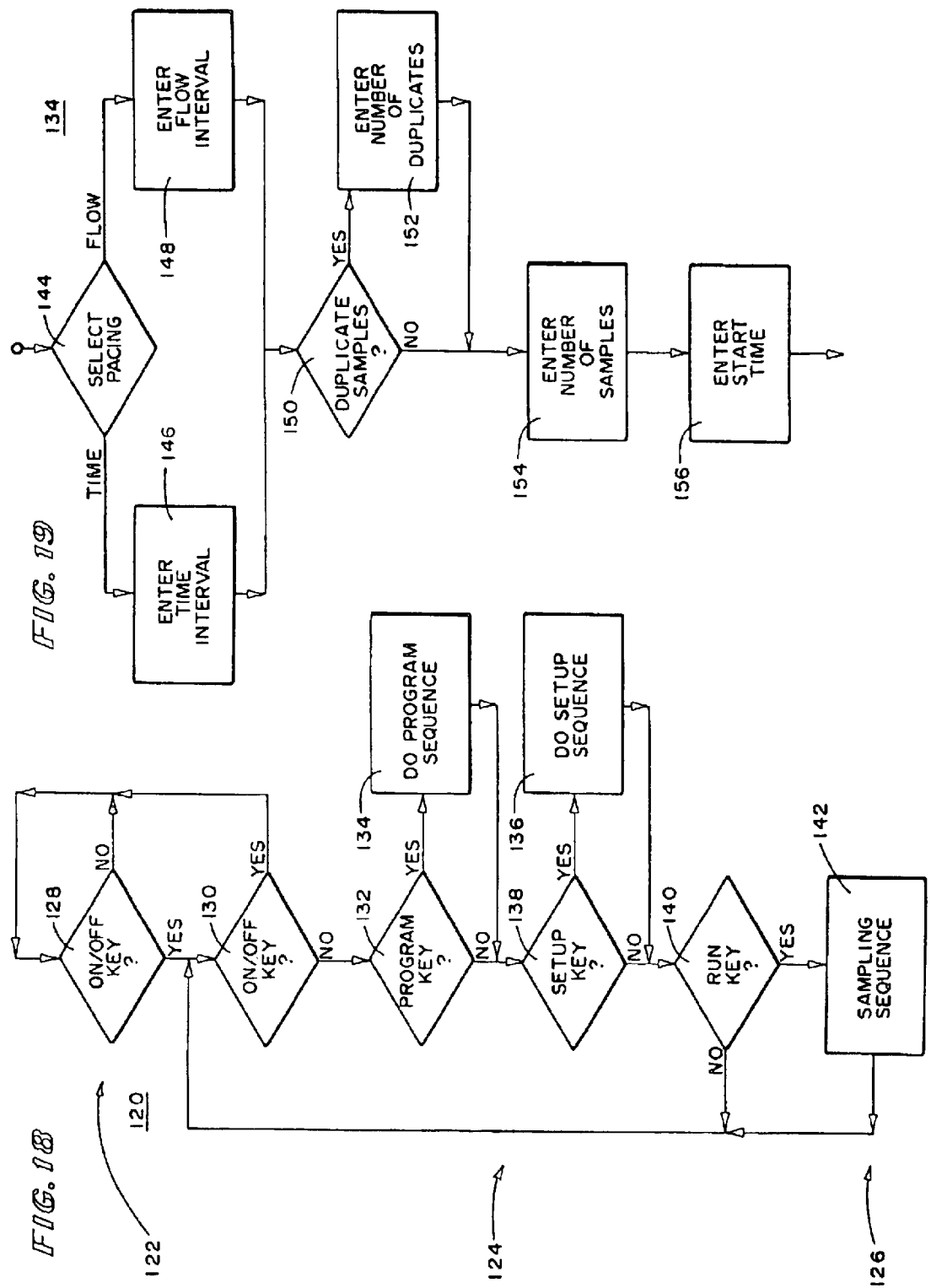

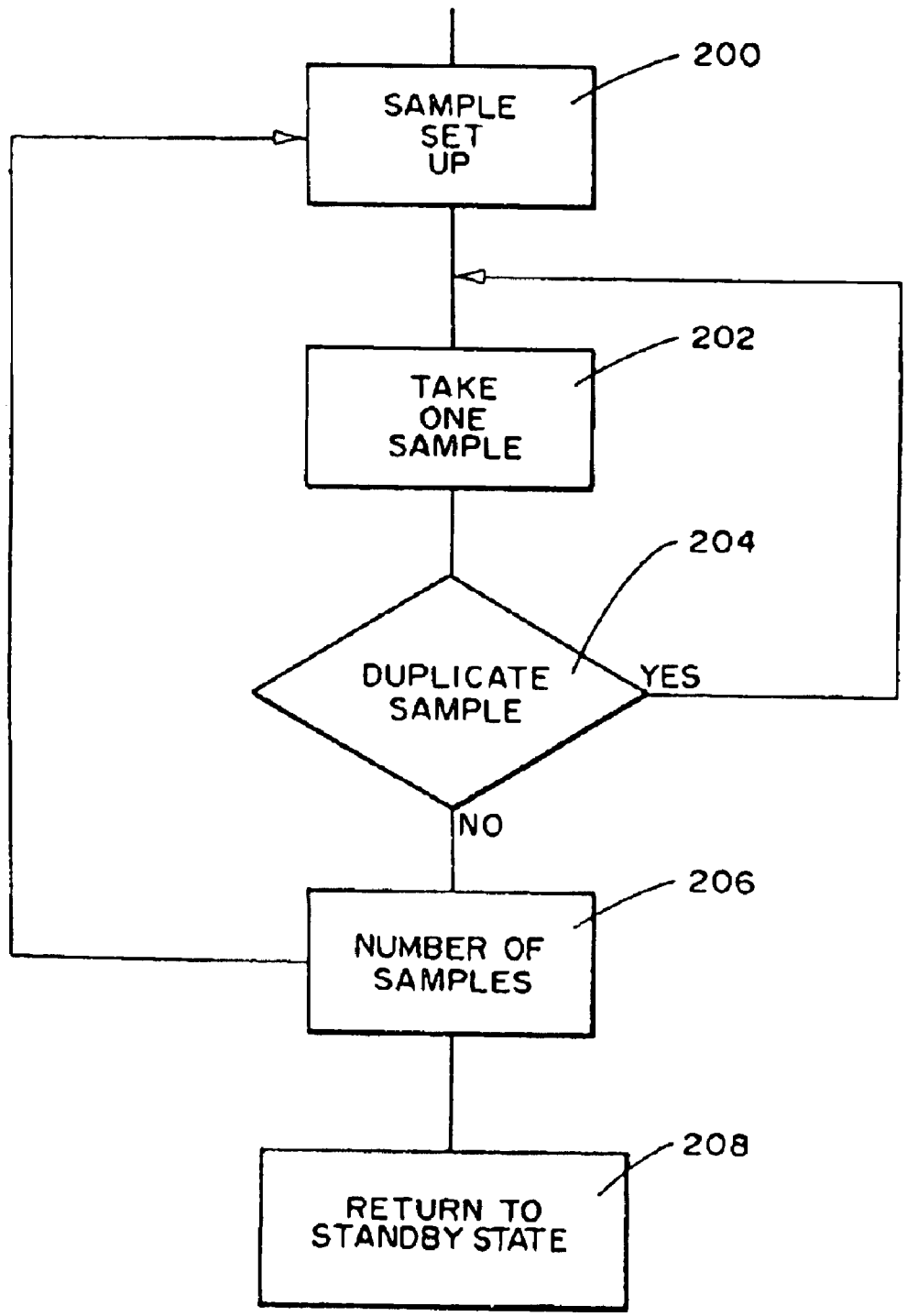

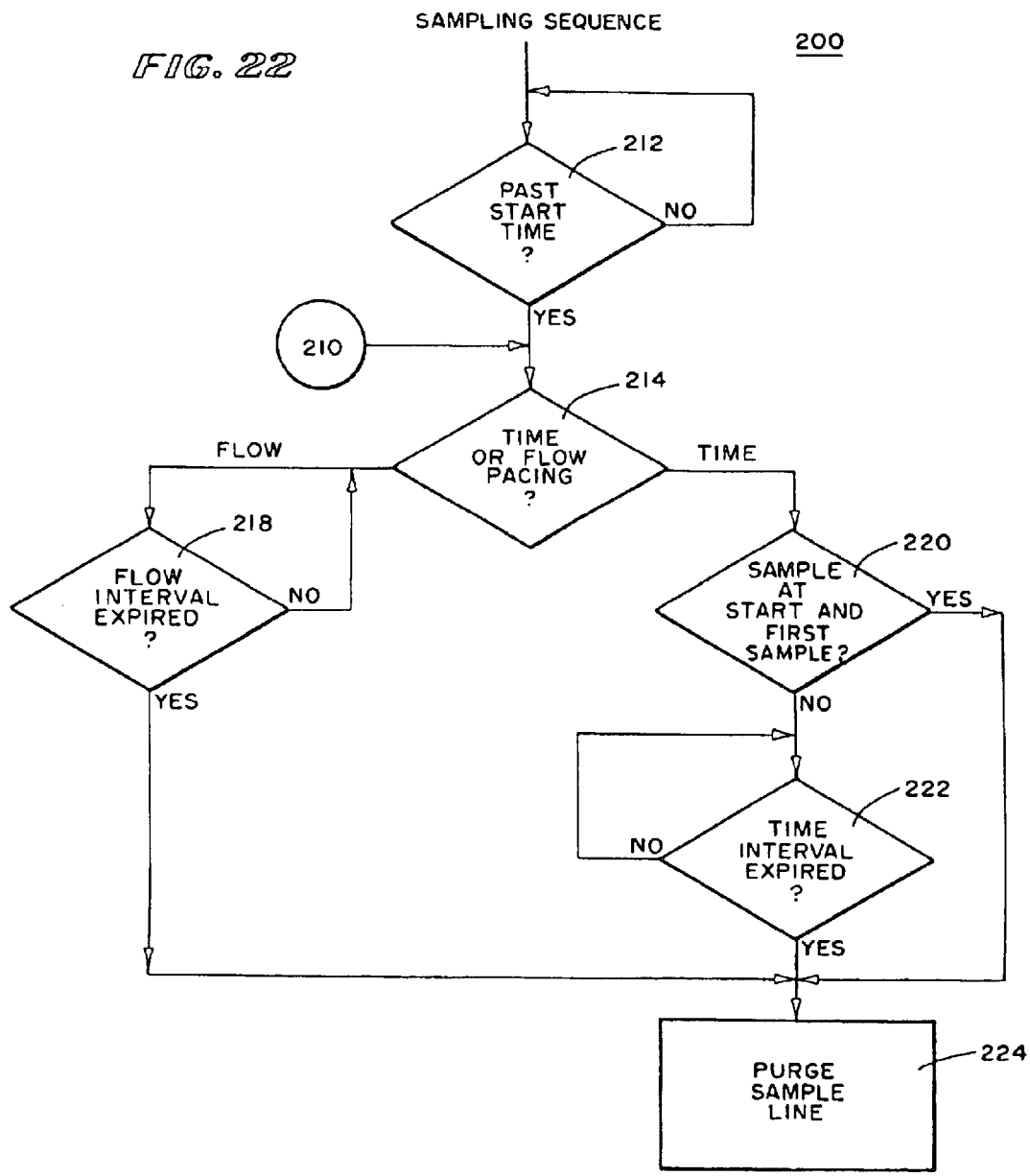

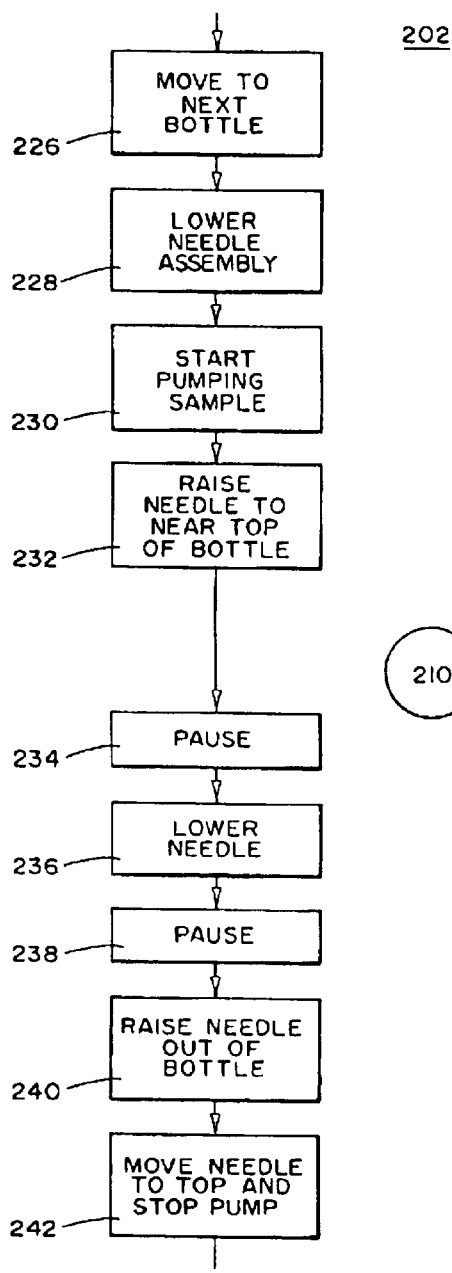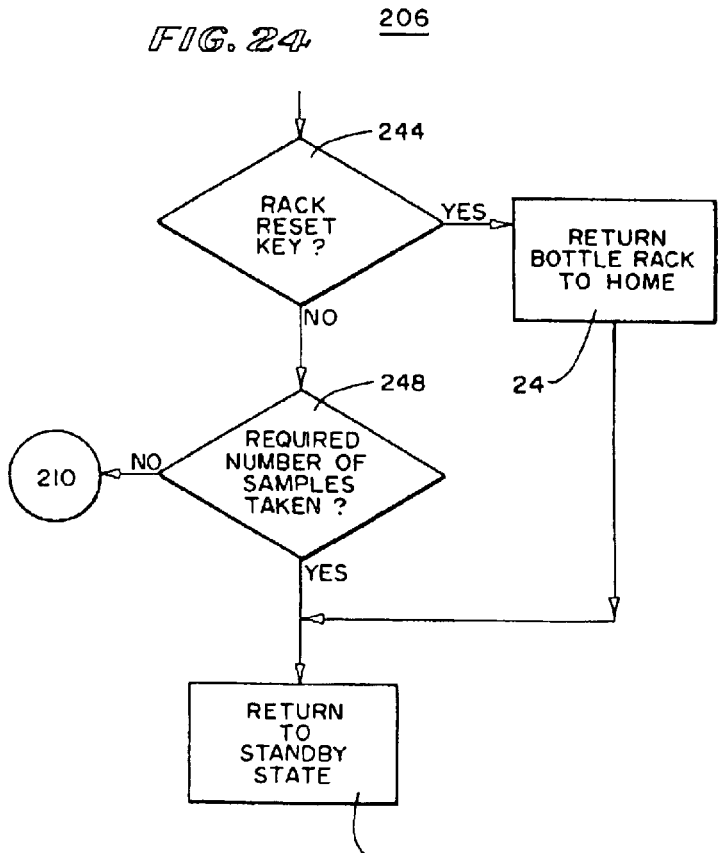

SAMPLER

REFERENCE TO RELATED APPLICATIONS

This application is a continuation-in-part application of U.S. application Ser. No. 09/570,900, filed May 15, 2000, now U.S. Pat. No. 6,494,331 which is a division of parent application Ser. No. 08/040,117 filed Mar. 30, 1993, now U.S. Pat. No. 6,152,189 entitled SAMPLER by Paul G. Wright, et al., and assigned to the same assignee as this application.

BACKGROUND OF THE INVENTION

This invention relates to methods and apparatus for sampling liquids under conditions that maximize precise analysis of ingredients.

In one class of methods and apparatuses for sampling liquids, the apparatus automatically draws samples of known amounts of liquids at preprogrammed intervals and deposits them into containers, which are usually bottles. The prior art automatic samplers of this class fill open containers. This type of automatic sampler has a disadvantage if used to sample liquids with volatile materials in them because substantial amounts of the volatile materials escape before measurement.

Another class of sampler includes containers that can be opened to receive liquid and closed after filling without air space within them to preserve as much of the volatile materials that are within the liquid before being drawn as possible. A prior art type of sampler of this class includes a valve in an inlet conduit and a valve in an outlet conduit. This type of valve has a disadvantage in that it is difficult to automate because of the number and types of valves, the size of the valves and the size of the plumbing associated with the valves. A system of this type is disclosed in U.S. Pat. Nos. 4,974,456 and 4,864,877.

SUMMARY OF THE INVENTION

Accordingly, it is an object of the invention to provide a novel liquid sampler.

It is a further object of the invention to provide a novel automatic liquid sampler that can preserve representative samples of liquids having volatile materials in them.

It is a still further object of the invention to provide sample containers having a single opening that serves as the inlet port, overflow port and as a closure for the containers wherein there is no air space and only liquid in a filled container after sampling.

It is a still further object of the invention to provide a novel sampler that automatically draws samples and deposits them in containers with no air space in the containers.

It is a still further object of the invention to provide a novel sampler that does not release volatile materials from the liquid so that the liquid in the container is representative of the sampled liquid.

It is a still further object of the invention to provide a volatile liquid sampling system that only requires one valve for each container to fill it so that there is substantially no air space.

It is a still further object of the invention to provide an automatic sampling system in which a needle is passed through a valve opening to fill the container to overflowing and then withdrawn, with the valve opening being closed immediately upon withdrawal.

It is a still further object of the invention to provide a sample collecting system in which a needle is within a socket with a portion of it sealing a central outlet of the socket while the lines are purged and then the needle moves through the central opening of the socket into a bottle cap connector and valve opening to deposit a sample in a container.

It is a still further object of the invention to provide an automatic sampling system that samples hot liquids without losing volatile materials through bubbling.

In accordance with the above and further objects of the invention, a filling station sequentially fills sample containers by moving a hollow needle into each container in sequence and completely filling each container with liquid. The needle is moved into each container by moving it through a valve dedicated to that container. After purging air from the container where this is part of the procedure, the needle is withdrawn, preferably from near the bottom of the container, as liquid flows: (1) radially outwardly from the needle to sweep bubbles from the walls of the container and needle; and (2) under the liquid in the container to avoid turbulence that otherwise could release volatile compounds.

As the needle approaches the valve before filling, the valve begins to open and a fluid socket closes the bottle cap. The shank of the needle and an end ball or plug on the end of the needle slide through the fluid socket, a cavity on the bottle cap and through the valve opening. It proceeds to a location near the bottom of the container and injects sample. The bottle may be filled with liquid for displacing air and the needle withdrawn, with liquid continuing to flow as it is withdrawn. As the needle is withdrawn, the valve outlet closes. The opening and closing of the valve, the movement of the hollow needle, the insertion and removal of the socket from a connector in the bottle, the pumping of liquid and the movement of bottles into and from a filling station are all synchronized to provide samples precisely representing the liquid in the aquafer or other body of water, or other liquid being sampled.

In the preferred embodiment, the valve closes by rotating, with the valve being opened when the valve inlet is facing upwardly toward the needle, and being closed when it turns so that it is sideways. Just before the needle tip is inserted, during the time the container is being filled and for a short period of time after the needle is withdrawn, the fluid socket closes the container cap and any overflow liquid flows out of the connector. As the valve closes, there is a head of liquid above the valve so that no space for air or other gas is possible in the closed container.

When the socket is over the cap of a container with the needle extending through the valve opening, the socket seals the cavity in the cap and liquid fills the container from the needle. Liquid overflowing the container passes through the valve and into the socket where it leaves the outlet port. When the container has been filled and the needle withdrawn through the container valve opening to seal the central outlet of the socket, the socket can be withdrawn without releasing liquid to fall in the container.

At programmed intervals, different containers and at least one sampling station are moved with respect to each other and samples are taken to fill the containers. The containers are filled so that there is no head space and minimum loss of volatile compounds. Preferably, the containers are standard sample bottles. The containers are preferably open to the atmosphere for no more than a few seconds and should not be open for more than ten minutes during the entire operation to avoid contamination.

In some applications, samples are taken from liquid bodies at high temperatures. It has been found that upon cooling in a closed container, bubbles are formed, probably because a vacuum is formed in the sample bottles by the contraction of the liquid upon cooling. The vacuum may pull volatiles from the liquid to form bubbles. To prevent the formation of bubbles, samples are cooled before being sealed in the sample bottles or other container.

From the above description, it can be understood that the sampler of this invention has several advantages, such as: (1) it is completely automatic; (2) it can draw samples without substantial release of volatile compounds; (3) it can draw samples at predetermined intervals without human intervention; (4) a single valve permits the flow into a sample container, overflow from the container during purging of air and collection of the sample liquid in the container; (5) the liquid enters the containers with little turbulence that otherwise would cause the volatile compounds to be released before the container is filled and sealed; (6) samples drawn from hot bodies of liquid are cooled to reduce the incidence of bubbles of volatile materials being formed in the closed containers; and (7) the containers are completely filled with sample without head space.

SUMMARY OF THE DRAWINGS

The above noted and other features of the invention will be better understood from the following detailed description, in which:

FIG. 2 is a simplified, partly broken away, fragmentary view of a sampling device in accordance with the invention;

FIG. 3 is a plan view of a portion of the sampling device of FIG. 1;

FIG. 4 is a fragmentary front elevational view, partly sectioned of a filling station for sampling containers usable in the sampler of FIGS. 1–3;

FIG. 5 is a side elevational view, partly sectioned, of a container usable in the embodiments of FIGS. 1–4;

FIG. 6 is a top view of the container of FIG. 5;

FIG. 7 is a fragmentary sectional view of the container taken through lines 7—7 of FIG. 6;

FIG. 9 is an elevational view of a needle assembly useful in the embodiments of FIGS. 1–8;

FIG. 10 is an elevational view of a hollow needle useful in the embodiment of FIG. 9;

FIG. 11 is a sectional view of a bladder pump useful in some embodiments of samplers;

FIG. 14 is an exploded, fragmentary, partly broken away diagram of a portion of the embodiment of FIG. 12;

FIG. 17 is a perspective exploded view of another embodiment of filling station similar to the embodiment of FIGS. 8–10;

FIG. 18 is a block diagram illustrating the software steps utilized in sampling liquid in the embodiments of FIGS. 1–10;

FIG. 19 is a block diagram of a portion of the program of FIG. 12;

FIG. 21 is a block diagram of still another portion of the program of FIG. 12;

FIG. 22 is a block diagram of a portion of the program of FIG. 19;

FIG. 23 is a block diagram of another portion of the program of FIG. 19; and

FIG. 24 is a block diagram of another portion of the program of FIG. 19.

DETAILED DESCRIPTION

Figure 1:
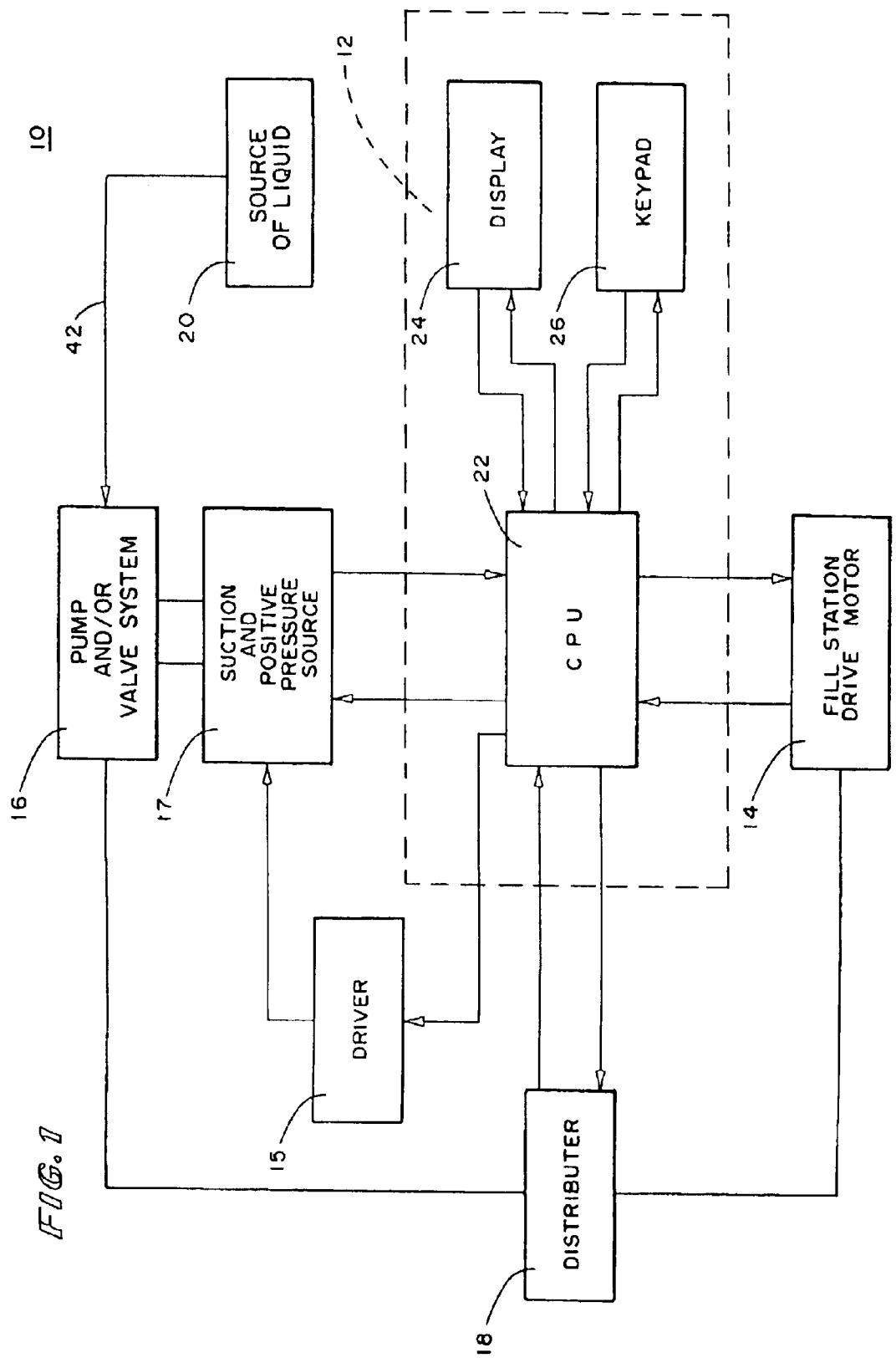
FIG. 1 is a block diagram of a sampling device in accordance with the invention.

In FIG. 1 there is shown a block diagram of a sampler system 10 having a control system 12, one or more fill station drive motors 14, a pump and/or valve system 16, a driver for the pump and\or valve system 16, and a distributor 18. The pump and/or valve system 16 is adapted to communicate with a source 20 of liquid to sample the liquid therefrom. A valve system may be used when pressurized air from an external source is provided to power a pump or the source 20 of the samples is already under pressure sufficient to move the samples to the distributor 18. While a bladder pump has some useful characteristics for some applications, any known mechanism for drawing samples may be used in the pump and/or valve system 16 including for example a peristaltic pump, gear pump or source of pressure from gas or gravity. While the pump and/or valve system 16 may include any type of pump or other mechanism for supplying the sample, it is advantageous for it to be a pump or other mechanism that draws liquid without such force as to dislodge volatile materials from the liquid.

The control system 12 can be preprogrammed to cause the pump and/or valve system 16 to supply samples of water from the source 20 of liquid to containers within the distributor 18 and to control the fill station drive motor 14 to fill containers, which are usually standard sample bottles within the distributor 18. The control system 12 controls this operation to automatically fill a series of containers with no air spaces remaining in the containers.

The control system 12 includes a central processing unit 22 with a typical display and/or printing unit shown at 24 and typical input units such as a keypad or electrical communication jack shown at 26. The control system 12 is programmed and contains the necessary interfaces to coordinate the operation of the pump and/or valve system 16, the distributor 18 and fill station drive motor 14 in such a way as to provide flexibility in drawing samples. It coordinates the operation of the individual components to properly fill containers while maintaining the integrity of volatile substances within the liquids for later testing.

In FIG. 2, there is shown a fragmentary, partly broken away, elevational view of a sampling system 10 enclosed within a sampler housing 30. The view is broken away to expose an outlet conduit from the pump 16 (FIG. 1) and a portion of the distributor 18. A conduit 28, shown broken away in FIG. 2, communicates at one end with an overflow opening 29 within the distributor 18 to receive overflow liquid and channel it back to the source of fluid or other location through a drain 31.

The pump and/or valve system 16 (FIG. 1) communicates through a conduit 40 and with a source of sample and through a conduit 42 to the filling station 32 within the distributor 18 to supply the liquid to the distributor for insertion and storage in the containers. The containers are filled completely with liquid so there is no air space and are closed before and after filling with liquid. The conduits 40 and 42 and the interior of the pump are made of inert materials that do not impart impurities to the liquid nor absorb ingredients of the liquid so the sample is preserved for testing.

The distributor 18 includes a filling station 32, a container rack drive 36, and a container rack 38 adapted to position any of a series of containers such as the container assemblies 34A–34C within the filling station 32 in sequence for receiving liquid. The container assembly 34A is shown in position to receive liquid in FIG. 2. Generally, a circle of containers are on the container rack 38 to enable a series of samples to be drawn and deposited in different containers although only three are shown in FIG. 2 for illustration.

In the preferred embodiment, the container rack drive 36 rotates the container rack 38 to move the containers into the filling station 32, although obvious alternatives could be used, such as moving the filling station 32 or instead of using one filling station using a plurality of filling stations which in a programmed way receives samples. While more than one filling station may be used and more than one arrangement of containers and filling stations may be used, for simplicity, one filling station and a single rack 38 for moving a series of circularly-spaced-apart containers into the filling station are described herein, one filling station being shown in FIG. 2.

To receive and fill containers, the filling station or tower 32 includes a moving section 50, a stationary section 52, the central processing section 22 and a drive section. The drive section is indicated generally at 54. The drive section 54 includes a motor 80 below the level of the container rack 38. The stationary section 52 supports the moving section 50 which moves a needle assembly 62 into containers under the control of the drive section 54.

The moving section 50 includes a spring-biased cam follower 60, a valve grip 61, the needle assembly 62, a top frame 66, and a downwardly extending cam shaft 68. The cam shaft 68 is connected to the top frame 66 for movement therewith. The needle assembly 62 includes a cage formed of posts 87A, 87B and 87C (87A and 87C being shown in FIG. 2), a hollow needle 83, a socket or fill tip 97 having an overflow port 29 and a spring 93. A drive screw 82 moves the top frame 66 up and down to move the hollow needle 83 within a cage formed of posts 87A–87C of the needle assembly 62 through the valve 64A (FIGS. 5–7). The valve 64A is opened by the cam follower 60 to permit the hollow needle 83 to pass therethrough. The cam follower 60 is turned as the top frame 66 and cam shaft 68 move.

To open the valve 64A, the cam follower includes at one end the bifurcated valve grip 61 mounted to the cam follower 60 through a shaft 63 so that a valve handle fits within the grip 61 and is turned to open the valve when the hollow needle 83 is within the valve opening and close the valve when the hollow needle 83 is not within the valve opening. The valve handle is horizontal when the valve is closed and vertical when open.

When the hollow needle 83 is near the bottom of the container assembly 34A, liquid is pumped through outlets near the tip of the hollow needle 83 which permit the fluid to flow laterally, slowly and gently outwardly to fill the container and cause it to overflow in an air purging operation. Liquid continues to flow after purging and the hollow needle 83 is withdrawn through the liquid while still ejecting liquid from its lateral outlet ports. When the hollow needle 83 is clear of the valve opening, the valve closes under the control of the cam follower 60 in a manner to be described hereinafter. In this specification, the word, "slowly" and the word, "gently" each mean sufficiently slow or gentle to avoid turbulence that could cause volatile material to be released.

To move the container assemblies 34A–34C into the filling station 32 for filling, the container rack drive 36 includes a distributor motor 70, a transmission 72, a shaft 74 and an optical encoder switch 76. The motor 70 drives the shaft 74 through reducing gears in the transmission 72.

To accurately position the container assemblies 34A–34C for receiving the hollow needle 83, the shaft 74 has mounted to it at its lower end an optical encoder disk 78 for rotation therewith. As the disk 78 rotates, the photocell switch 76 senses indicia on the optical disk encoder at increments related to the circumferential spacing of container assemblies 34A–34C on the container rack 38 to terminate movement of the rack when the container assemblies 34A–34C are properly positioned for filling. The motor 70 remains stationary until started by the control system 12 to move a full container out of the filling station while moving an empty container into the filling station.

The container assemblies 34A–34C each include a corresponding one of the containers 92A–92C, a corresponding one of the valved container caps 90A–90C and a corresponding one of the container stations 91A–91C, each of which has a curved outer wall portion and post to receive a container.

The containers 92A–92C fit within and are removably held within the container stations 91A–91C and are closed by the valved container caps 90A–90C, with the valve being closed except during a filling operation. They are generally standard 40 milliliter vials of glass with a custom made valved-cap made of an inert material. In the preferred embodiment, the inert material is Teflon. (Teflon is a trademark for tetrafluoroethylene owned by DuPont de Nemours, E.I. & Co.; Wilmington, Del. 19898).

In FIG. 2, the cam shaft 68 is shown engaging the cam follower lever 60 just before it turns the bifurcated valve grip 61. The valve grip 61 includes an opening 107 sized to grip the container cap valve end in a manner to be described hereinafter when the container is in the filling station 32. With this arrangement, as the horizontal platform 66 moves downwardly, the cam shaft 68 moves the lever 60 and causes the valve grip 61 to rotate and thus open the valve in the container cap.

In FIG. 3, there is shown a container rack 38 mounted for rotation with the drive shaft 74 (FIG. 2) and containing circumferentially spaced around its periphery, a plurality of container stations 91A–91Y for holding a plurality of sample containers with special valved-caps such as shown in FIGS. 5–7.

The rack 38 is adapted to move the containers into the filling station 32 one by one with valve handles positioned to fit within the bifurcated valve grip 61 (FIG. 2). For example, in FIG. 3, the container station 91A is shown within the filling station 32 positioned to hold a container 90A (FIG. 2) that is to receive liquid.

The rack 38 is a cylindrical disk with a flat circular upward section and marked compartments each having a different one of the container stations 91A–91Y spaced in accordance with the program in the control system 12 (FIG. 1) to be moved in a predetermined sequence into the filling station 32. The stations include curved outerwalls with corresponding slots 89A–89Y in them to receive valve handles 99 of the containers and corresponding inner posts 113A–113Y with a corresponding one of the center raised supports 81A–81Y for the containers. The inside of the rack may include ice.

The rack may be easily removed and replaced if desired. One compartment may contain a container sent from the laboratory with a prefilled standard liquid and the computer may be programmed not to fill it. Moreover, a second fill station 18A may be used to insert preservatives or the like before filling with sample. The location of the standard may be programmed into the computer but otherwise not known to the operator to provide a blind test by preventing field personnel from altering a measurement.

In FIG. 4, there is shown a partly-sectioned fragmentary front elevational view of a sampling system 10 with a filling station 32 shown in greater detail mounted to receive container assemblies (not shown in FIG. 4). As best shown in this view, the stationary section 52 includes four posts, three of which are shown at 84, 85 and 86 mounted in and supporting in a top horizontal platform 67 for the central processing unit 12.

The movable section 50 (FIG. 2) includes a movable horizontal plateform 66 internally threaded to receive a power screw 82 for movement by a motor 80 downwardly and upwardly as the motor 80 rotates to turn the screw 82 in either counterclockwise or clockwise direction. The needle assembly 62 and the downwardly extending cam shaft 68 are mounted to the horizontal platform 66. The cam shaft 68 engages the cam follower 60 and moves it to open and close the valve 64A (FIG. 2) in a manner to be described hereinafter.

The needle assembly 62 includes a hollow needle 83, a fluid socket 97 and a spring biased cage 87 to be described hereinafter, with the hollow needle 83 being aligned to pass through the valve opening in the valve 64A (FIG. 2). With this arrangement, a container is moved into position and the control system 12 (FIG. 1) causes the motor 80 to drive the screw 82 through a predetermined distance downwardly. As it moves downwardly, the downwardly moving cam shaft 68 engages the cam follower 60 to rotate the valve 90 degrees so that the valve opening is positioned upwardly to receive the hollow needle 83 which then passes downwardly into the container. The cam follower 60 includes a lever pivoted about the pivot point 69 and spring biased upwardly by a spring 71 to close the valve 64A unless the cam shaft 68 depresses the end of the cam follower.

When the power screw 82 has moved the movable section 50 (FIG. 2) its full distance, it stops for the bottle filling operation to displace air and then reverses direction. In coordination with the insertion and removal of the hollow needle 83, the control system 12 causes liquid to be pumped into the container (not shown in FIG. 4). The valve opening is sized to pass the ball 103 with a slight clearance and to have a slightly larger clearance for the hollow needle 83.

As the hollow needle 83 and the cam shaft 68 (FIG. 2) move upwardly, the cam follower 60 is released and the valve spring 71 rotates the valve opening to close the container. The container is open through the valve opening preferably for less than five seconds after the needle clears the valve and in the preferred embodiment for one or two seconds. It should not be open for more than ten minutes to avoid receiving substantial contaminants such as gas from the air and to avoid releasing volatile gases from the sample into the air. The liquid level is kept above the openings 114 in the needle while liquid flows from the needle. It is also pumped fast enough so that by the time the needle is removed from the container the volume of liquid pumped into the container has been equal to four times the volume of the container.

The needle assembly 62 includes a tubular cage 87, a helical compression spring 93, the hollow needle 83 and an end needle ball or plug 103. The cage 87 confines the compression spring 93, which biases the cage 87 downwardly, so that it extends from the backing plate 66 until it is forced against the container cap at which time, it moves upwardly while the hollow needle 83 continues downwardly through the valve into the container.

The needle 83 is centered in the cage 87 with the spring 93 around it and communicates with the source of sample at its upper end. The plug 103 is a spherical body aligned with the central opening of the hollow needle 83 to form a liquid seal in the fluid socket 97 central opening but sufficiently small in diameter to pass through the valve opening. It is sized to seal the fluid socket central opening when the needle 83 is retracted, with the tapered end of the socket 97 at the bottom of the cage 87 fitting around a container cap to sealingly receive the valve body 90 (FIG. 5) of the container cap.

In FIG. 5, there is shown an elevational view of a container 92 and valved-cap 90, with the valved-cap 90 having internal threads adapted to engage external threads on the container 92 for a tight fit. The valved-cap 90 has an upwardly extending portion through which a valve shaft 98 rotatably passes in a transverse direction. The valve shaft 98 is generally cylindrical to permit rotation within the cap but includes a flat end or valve handle 99 that removably fits within the opening 107 (FIGS. 2 and 4) of the valve grip 61. With this arrangement, the valve grip 61 receives the shaft end or valve handle 99 when the container 92 is moved into the filling station 32 (FIGS. 2–4). The valve is closed when the bifurcated grip 61 (FIGS. 2 and 4) receives the horizontally positioned valve handle 99.

When the downwardly extending cam shaft 68 (FIGS. 2 and 4) engages the cam follower 60 (FIGS. 2 and 4) and moves it, the valve grip 61 is turned so as to rotate the valve handle 99 and shaft 98 through 90 degrees. The 90 degree rotation is timed so that it is complete just as the hollow needle 83 (FIGS. 2 and 4) approaches the valve. This synchronization is accomplished by the position of the cam shaft 68. Similarly, as the cam shaft 68 moves upwardly past the cam lever 60, the cam lever 60 pivots and the valve grip 61 is rotated by the bias from spring 71 (FIG. 4) to close the valve. The valve opening and the portion of the shaft near it are below the level of the liquid in opening 96 when the valve closes, so that the container is not exposed to atmosphere through the valve.

To receive the needle assembly 62 (FIGS. 2 and 4) with its hollow needle 83 (FIGS. 2 and 4), the cap 90 is sized and shaped to fit within the socket 97 (FIGS. 2 and 4) in the preferred embodiment. It includes in its center an upwardly extending funnel shaped cavity 96 that communicates with passageway 101 within which the valve shaft 98 is positioned. The passageway 101 communicates with the interior of the container through the valve opening 100 in the valve shaft 98 when the valve is open.

In another embodiment (not shown), the end of the needle assembly cage 87 is complimentary to the shape of the funnel-shaped opening 96 and the end of the cage 87 seals against the container cap by fitting within the cavity 96. In this embodiment, the hollow needle 83 moves from the tip of the cage 87 through the valve opening and into the container in the same manner as the embodiment of FIG. 5.

The valve shaft has the opening 100 positioned so that the cavity 96 and the valve opening 100 are in communication in one position of the shaft to permit the needle to pass therethrough, and in another position, the valve shaft is turned to block communication between the cavity 96 and the container.

In FIG. 6, there is shown a top view of the valved-cap 90 showing the manner in which the valve 64A and shaft 98 pass through the upwardly extending valve opening or cavity 96 (FIG. 5) with the small hole 100 through the shaft 98 having a diameter substantially the same size as the diameter of the needle ball or plug 103 (FIG. 4) on the end of the hollow needle 83 (FIG. 4) so that the needle assembly 62 (FIGS. 2–4) fits into the opening 96 (FIG. 6) and the hollow needle 83 and needle ball or plug 103 passes through the opening 100.

In FIG. 7, there is shown a fragmentary sectional view taken through lines 7—7 of FIG. 6 showing an upper portion of the container wall 92 and the Teflon cap 90 with the shaft 98 extending through the upward portion of the cap 90 through the passageway 101 that connects the interior of the container with the funnel shaped cavity 96 so that the open portion 100 of the shaft 98 is aligned with the narrow diameter passageway 101 of the cap 90 sized and shaped to permit the hollow needle 83 (FIGS. 2 and 4) to pass through it with some clearance. The upward section of the cavity 96 is funnel-shaped to form a reservoir when the socket 97 of the needle assembly 62 seals itself around the bottle cap as the needle moves downwardly. The end portion 99 has been turned 90 degrees.

The cap 90 is threaded onto the container by internal threads 105 on the cap and complementary external threads on the container neck. It includes a thin flexible flange 119 and an O-ring such as 102. The "O" ring 102 exerts an even pressure on the flange 119 to maintain and distribute force and thus seal the flange against the bottle top even though the bottle top may not be smooth and level. The containers are adapted to fit in a holder in a ring of holders on the distributor 18 (FIG. 2) to permit ease of insertion. Moreover, the distributor 18 can be easily removed and the sealed containers with sample can be sent as an entity to be tested, if desired.

In the preferred embodiment, the handle 99 has a heighth of 0.375 inch and should not be smaller than 0.100 inch nor larger than 0.750 inch in heighth and has a length of 0.62 inch and a width of 0.375 inch. The valve opening 100 has a diameter in the preferred embodiment of 0.188 inch and should not have a diameter lower than 0.150 inch or larger than 0.500 inch.

The inner edge of the socket 97 should not be smaller than 0.500 inch nor greater than 0.800 inch. In the preferred embodiment, it is 0.670 inch. The opening 107 in the bifurcated gripper 61 should have a heighth no smaller than 0.125 inch nor greater than 0.625 inch. It preferably has a heighth of 0.380 inch. Generally, it is circular and has a diameter of 1 inch. The diameter of the bifurcated gripper 61 should be no smaller than 0.500 inch nor greater than 1.5 inches.

The diameter of the widest portion of the funnel-like cavity 96 is 0.0530 inch and narrows down to the diameter of the passageway 101. The passageway 101 in the preferred embodiment is 0.188 inch in diameter and should be no smaller than 0.050 inch nor larger than 0.500 inch in diameter. The diameter of the cap in the preferred embodiment is 0.850 inch and should not be narrower than 0.700 inch nor larger than 0.950 inch. It is generally cylindrical to have a circular cross section from the top.

Figure 8:
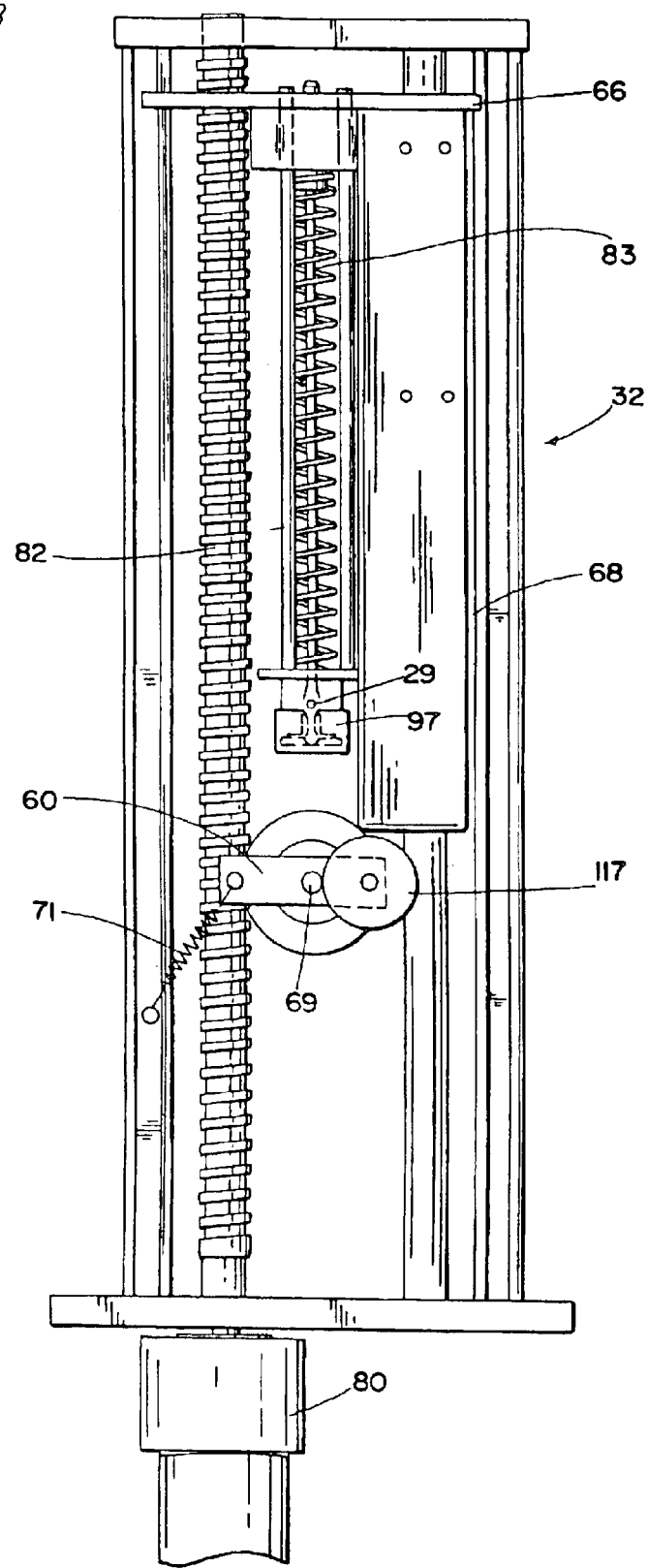
FIG. 8 is a rear fragmentary, elevational view of the filling station of FIGS. 1–4.

In FIG. 8, there is shown a rear, fragmentary elevational view of the filling station 32 showing the downwardly extending cam shaft 68, the cam follower 60, the spring 71 and the hollow needle 83. This mechanism turns the bifurcated grip 61 (FIGS. 2 and 4) in synchronism with the entry of the needle 83 into the valve and with the exit of the needle from the valve so that the interior of the container and atmosphere do not communicate for an unduly long time.

As the platform 66 moves downwardly, moving the needle 83 into the entrance of the container, the cam shaft 68 engages a roller 117 on the end of the cam follower 60 and moves the cam follower so it pivots about point 69 against the pressure of the spring 71 which is put in tension as the cam shaft 68 moves downwardly. This causes rotation of the gripper 61 about the pivot point 69 to turn the bifurcated member 61 and open the valve just as the tip of the needle 83 enters the valve opening 100 (FIGS. 5 and 7).

The cam continues downwardly, rolling on the roller 117 for the filling operation until the needle begins to withdraw and inject sample as it withdraws into the container. At this point in time, the shaft 68 moves upwardly but the roller 117 simply rolls against its vertical surface until the cam 68 begins moving above the horizontal and frees the roller 117. As it frees the roller 117, the spring 71 pulls the cam follower 60 and the bifurcated member 61 again rotates 90 degrees to close the valve.

In FIG. 9, there is shown an elevational view of the needle assembly 62 having a hollow tubular downwardly extending support housing or cage 87, a socket 97, an overflow outlet 29 in the housing of the socket 97, a shoulder 118 having elongated openings to loosely receive aligning rods 87A–87C of the cage 87, a nipple 116, a helical compression spring 93 and a needle 83. The nipple 116 is adapted to be engaged by the conduit 42 (FIG. 2) at its top and to communicate with the interior of the hollow needle 83 at its bottom within the shoulder 118.

The hollow needle 83 includes a plurality of radial openings 114 in its side walls and the end needle ball or plug 103 at its end. Holes 114 open radially to permit the liquid to be slowly and gently sprayed outwardly toward the walls as the needle moves between the bottom of the container and the top of the container and thus avoids the turbulance, agitation, or other inertial forces which may cause volatile material to be freed. The hollow needle 83 is generally and preferably of stainless steel.

The cage 87 is defined by guide rods 87A–87C that confine the spring 93 at an upper portion and walls forming a socket 97 with a cylindrical interior seal 95 that engages the container cap 90 (FIGS. 4, and 6–7), an insert 104 and the overflow outlet 29. The opening formed by insert 104 has a diameter smaller than the diameter of the end needle ball or plug 103 to be sealed thereby when the end needle ball or plug 103 is seated but larger in diameter than the hollow needle 83 to permit overflow liquid to flow upwardly and out to the overflow outlet 29 into the overflow tube 28 (FIG. 2). The spring 93 creates bias between sealing plate 109 and socket 97 to force the socket over the cap and to force the ball 103 into insert 104 and seal this socket. The reservoir 115 is defined by the walls of the insert 104, ball 103 and "O" ring 111. It is vented by drain 29.

The socket 97 is sealed by the ball 103 to permit purging of hoses without liquid flowing into the containers and to close the socket 97 against leakage while it is being withdrawn from or inserted onto the cap of a container or while it is between containers. The reservoir 115 is blocked by sealed plates 106 and 109 compressing on "O" ring 111 to avoid flow of liquid upwardly during a purge operation, or when liquid is overflowing the container. The posts defining the upper portion of the cage 87 extend upwardly beyond the shoulder 118 to permit compression of the spring 93 between the shoulder 118 and the plate 106 as the needle 83 moves downwardly. They are loosely mounted in holes such as 117 to permit movement laterally of the cage 87 for alignment of the socket 97 with the cap of the container. The socket moves laterally within a range of 0.002 inch and ⅛ inch of true position.

In FIG. 10, there is shown an elevational view of the hollow needle 83 having the nipple 116 on one end to receive a hose through which sample liquid is pumped, the support boss 117 through which it passes near the upper end for fastening to the moveable shoulder 118 (FIG. 9), an elongated hollow stem with openings 114 radially extending through its walls near the end and the plug or ball 103 at the very tip.

As shown in this view, the hollow needle 83 may be connected by a flexible hose or other member to a source of sample and moved downwardly and upwardly. The small holes 114 enable liquid to be gently ejected outwardly in a radial direction while the needle moves longitudinally. The end ball 103 serves as a plug to close the socket 97 so that liquid does not flow outwardly from the reservoir 115 on top of the container or distributor (FIG. 2) while the needle is being pulled upwardly such as between containers.

With this arrangement, the overflowing liquid when the hollow needle 83 is at the bottom, purges the container and the sides of the valve. While the hollow needle 83 is being withdrawn, the pattern of liquid, moving laterally outwardly and causing further overflow as the hollow needle 83 moves up, strips any bubbles that remain around the hollow needle 83 and the container while preserving the integrity of the liquid.

The container is only open while it is being filled and only slightly open at that point in time. The opening is actually closed by liquid flowing outwardly so that there can be no contamination and the gentle filling action avoids agitation that might cause the escape of a large amount of volatile material in the liquid. The liquid movement is adequate to force the bubbles of air free from surfaces by overcoming the adhesion forces but not so vigorous as to free volatile material in the sample. The containers are closed and transported in the container rack. The entire rack can be shipped. It is easily removed from the distributor.

In FIG. 11, there is shown a longitudinal sectional view of a bladder pump and/or valve system 16 having an air inlet port 150, a liquid inlet port 158 and a liquid outlet port 152. The air inlet port 150 is connected to the compressor 17 (FIG. 1) to receive pressure and vacuum alternately. The liquid inlet port 158 is closed by a spring biased valve element as part of a check valve 162 to permit the entry of liquid and prevent the exit of liquid or air, and the liquid outlet port 152 is closed by a check valve 164 to prevent liquid from flowing in but permitting it to flow out. The spring biased check valves permit the pump to be horizontal, vertical or any position between horizontal and vertical and still function.

A steel wall 156 circumscribes the pump with a coaxial bladder 160 being mounted inside of it and an apertured cage tube 154 being mounted along the longitudinal axis of the pump within the bladder 160. The wall 156, the bladder 160 and the cage 154 are all cylindrical tubes coaxial with each other to form a first cylindrical tubular passageway between the wall 156 and bladder 160 to receive air under positive pressure or suction air from the air inlet port 150, a second tubular cylindrical passageway between the inner cage tube 154 and a bladder 160 for liquid communicating with the liquid inlet port 158 and a third solid cylindrical passageway for liquid communicating with the liquid inlet port 158 and liquid outlet port 152.

In operation, vacuum or negative pressure is applied to the air inlet port 150 by the compressor 17 (FIG. 1) while the liquid inlet port 158 of the bladder pump is submerged. Liquid is pulled into the liquid inlet port 158 through a filter 157 and inlet port 158 past the check valve 162 as the bladder 160 is pulled toward the wall 156 by the vacuum pressure. Next, pressure is applied to the air inlet port 150 causing the bladder 160 to be pushed inwardly toward the cage 154, forcing liquid through the check valve 164, out of the liquid outlet port 152 and closing the check valve 162. These cycles are repeated.

With this arrangement, liquid can be pumped without substantial submergence of the pump so that it operates under low or substantially no head such as in very shallow liquid. Moreover, it can push a column of liquid from a depth deeper than 26 feet, such as for example as low as 80 feet or lower. The combination of exhaust and positive pressure increases the pressure head through which the liquid can be pumped and permits pumping at a faster rate, and reduces the time of pumping. The pumping rate is increased because liquid is pulled in faster. Moreover, the life of the bladder is increased because there are normally no tension forces on the bladder to stretch it since it is moved by pressure differentials rather than by stretching and releasing it. It should be no more than ten feet in length, and in the preferred embodiment, is two feet in length.

Drawing samples from hot liquids are frequently required in chemical process operations for environmental reasons. An embodiment of the invention is shown in FIGS. 12–15 for this purpose. One example application of this embodiment is in the paper and the pulp industry. In the preparation of paper, heated liquids are formed, particularly in the bleaching process, which contain toxic materials that must be measured.

Figure 12:
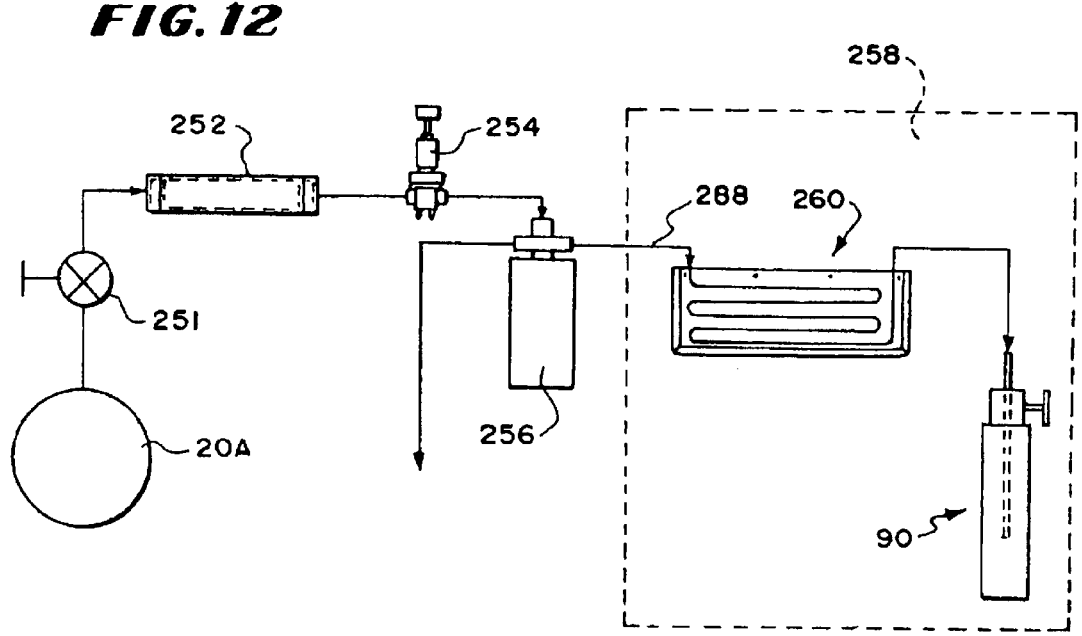
FIG. 12 is a schematic diagram of an embodiment for handling hot samples.

In FIG. 12, there is shown an embodiment 250 of apparatus for drawing samples from a heated body of fluid 20A having a maintenance shut off valve 251, a strainer 252, a pressure regulator valve 254, a purge by-pass valve 256 and a cooler housing 258. This embodiment is utilized to avoid bubbling in a sample container such as 90 when the samples are drawn from a hot body of water. Otherwise, under some circumstances, the cooling of the liquid in a vial such as 90 creates a vacuum pressure within the vial and this vacuum pressure causes bubbling from the liquid of certain volatile materials that are to analyzed.

To sample the hot liquids for analysis, the cooler housing 258 includes a ballast box 260 and the sampling apparatus of FIGS. 1–10 (not shown in FIG. 12), together with a plurality of sample vials, one of which is shown for illustration at 90 in FIG. 1. The ballast box 260 includes a ballast coil of tubing 288 that provides a residence time in the ballast box 260 before it is transferred to the containers such as 90 for collection, thus reducing the temperature of the heated liquid to a value of less than 84 degrees Fahrenheit and preferably to 40 degrees Fahrenheit. The coil is at least 15 feet long and preferably approximately 25 feet. The specific length of the ballast coil of tubing and temperature of the cooler housing 258 are selected to reduce the temperature of the liquid low enough to cool the liquid to below 40 degrees Fahrenheit in the preferred embodiment. The cooler housing 258 is held at a temperature lower than 40 degrees Fahrenheit for cooling but the exact temperatures are selected depending upon the particular liquids being sampled and the temperatures at which they are being sampled. The vials are preferably between 25 to 40 milliliters (mL) in inner volume with a screw on cap that includes a septum that is Teflon coated or coated with some other suitably inert material.

Figure 13:
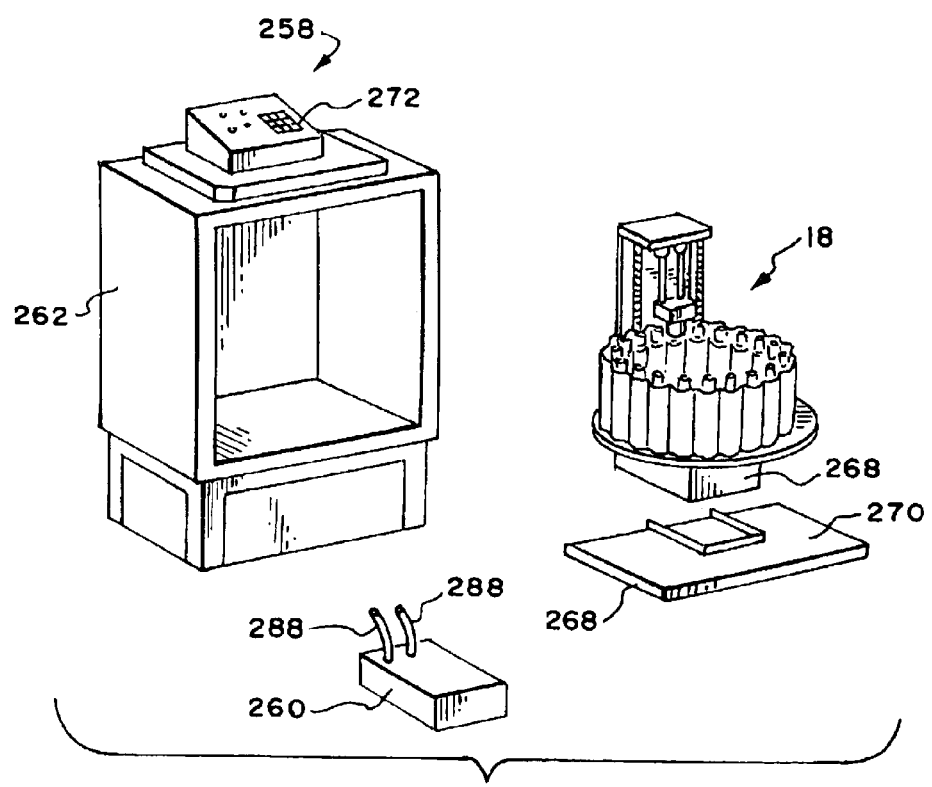
FIG. 13 is a simplified, perspective, partly-exploded view illustrating the embodiment of FIG. 12.

In FIG. 13, there is shown a simplified, perspective, partly-exploded view of a cooler 258 having a housing 262 that contains the distributor 18 in a top portion and the ballast box 260 and a housing 268 for the rack drive and motor for the distributor 18 for the sampling apparatus in a lower portion. The top portion and lower portion are separated by a panel 270. The control unit 272 is on top of the cooler. With this arrangement, hot samples may be drawn into the cooler housing 258, cooled and then distributed into vials at a temperature sufficiently low to avoid bubbling.

In FIG. 14, there is shown an exploded, fragmentary, partly broken away perspective view of a sample pre-cooler 260 having the housing 270, first and second parallel mounting bases 273 and 274, a first pair of first and second end guides 276A and 276B and a second pair of first and second end guides 278A and 278B for the ballast coil of tubing 288, first and second side guides 280 and 282 for the ballast coil of tubing 288, a seal 284 and the top support 286. The ballast coil of tubing 288 is wound in approximately seven loops over the end and center guides, with a first end 290 extending through the top support 286 and a second end 292 extending through the top support 286 where they are engaged by corresponding ones of the first and second fittings 294 and 296. With this arrangement, the ballast coil of tubing is wound within the pre-cooler 260 in a manner that permits substantial heat loss to a coolant within the ballast box. However, any suitable arrangement can be used to hold a ballast of tubing or other kinds of reservoirs that permit the liquid to be adequately cooled before it is applied to the containers.

To mount the top support 286 to the housing 270, ten nuts are spaced along the four side walls of the housing 270 on the interior surfaces with three being on each of the longs sides and two are each of the shorter end side, nuts 302A–302E being shown in FIG. 14. These nuts are fastened to the side walls with that tapped openings having a longitudinal axis vertical and parallel with the side walls. The ten nuts are aligned with ten openings 300A–300J along the edges of the top support 286 which rests on the upper edge of the side walls of the housing 270. The openings 300A–300J are arranged to receive screws which lit through the top support 286 and engage the nuts 302A–302J so as to hold the cover against the top edge of the housing 270. One such screw is shown at 308 aligned to fit through the opening 300J and others 300A–300I are shown within the top support 286. Each of the guides 276A–276B, 278A–278B 280 and 282 have central openings with the upper openings being aligned with different ones of the six openings 310A–310F in the top cover to receive screws, one of which is shown at 304 aligned with the opening 310D and others of which are shown in place. The bottom openings of the guides have similar openings aligned to match with screws 312A–312F in the parallel mounting bases 273 and 274 so that the guides are each held in place to receive a strand of the tubing 288. With this arrangement, the tubing 288 can be wound in approximately seven loops with the two ends extending through the fittings in the top support, one being connected from there to the hollow needle and the other being connected to receive the fluid.

Figure 15:
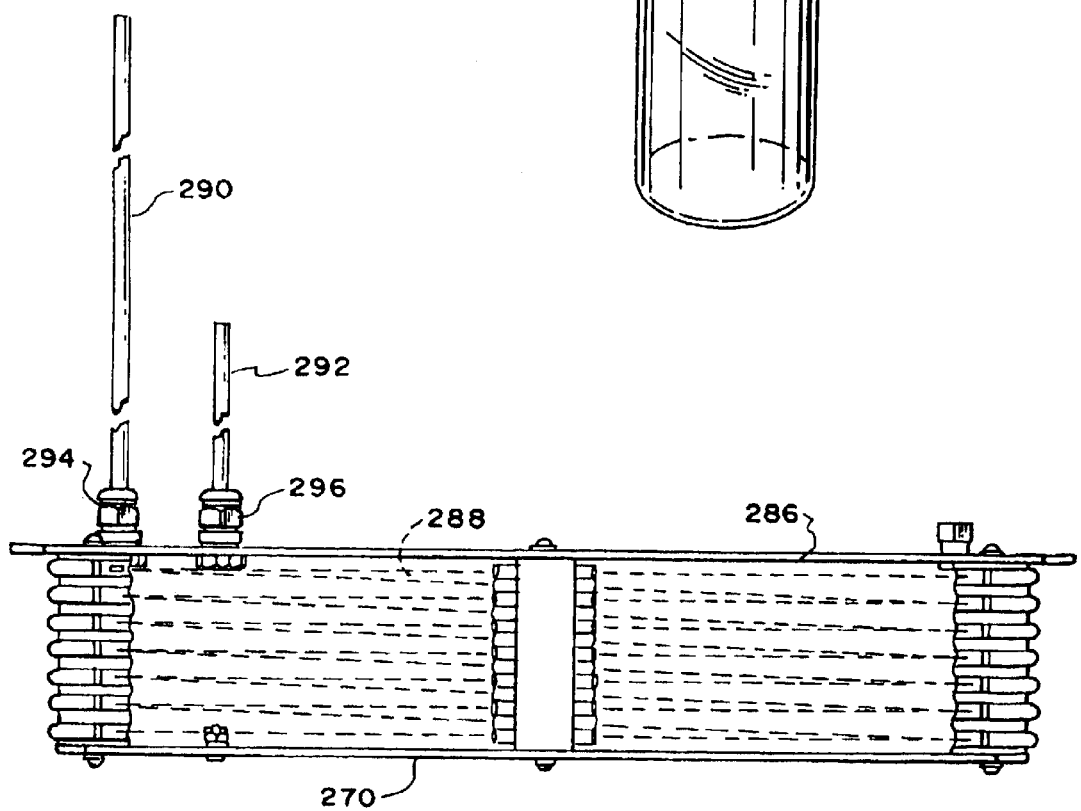
FIG. 15 is sectional, partly schematic drawing of a portion of the drawing of FIG. 12.

In FIG. 15, there is shown a partly schematic side sectional view of the sample pre-cooler 260 having a first end 290 to the ballast coil of tubing 288 and a second end 292 to the ballast coil of tubing 288 connected to the respective ones of the fittings 294 and 296 with the remainder of the ballast coil of tubing being wound on the first end guide 276A and second end guide 276B of the first pair of end guides and the first end guide 278A and second end guide 278B of the second pair of end guides and the first and second side guides 280 and 282 respectively in approximately seven full windings with the ends of the windings being 290 and 292 respectively.

Figure 16:
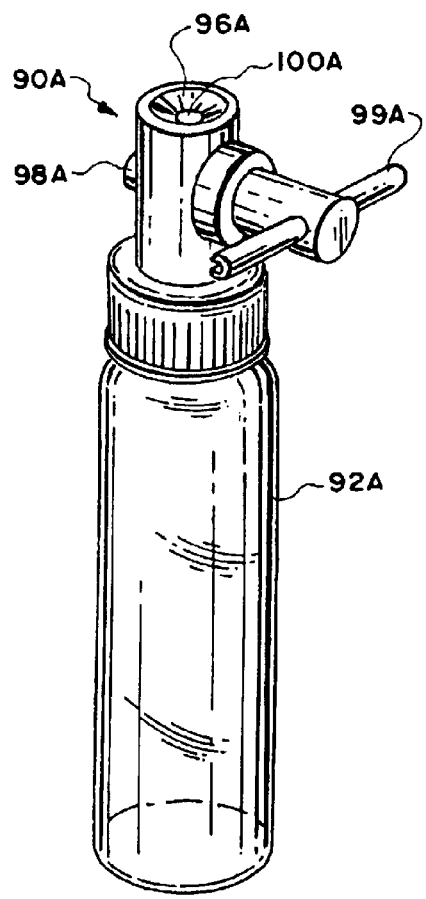
FIG. 16 is a perspective view of another embodiment of sample container similar to the embodiment of FIGS. 5–7.

In FIG. 16, there is shown a perspective view of another embodiment of sample container similar to the embodiment of FIGS. 5–7 having parts indicated with the same reference numeral followed with the suffix A. It operates in substantially the same manner but which utilizes a slightly different cam follower 99A as part of the valve. In the embodiment of FIG. 16, the cam followers are round cylinders that are automatically moved between the open and closed positions for the valve as the hollow needle enters the sample container through the funnel shaped cavity 96A and is retracted from it.

In FIG. 17, there is shown a fragmentary exploded perspective view of a valve actuator mechanism similar to the valve actuator of the embodiment of FIGS. 2–8 but designed to actuate the valve of the embodiment of sample container of FIG. 16. In the embodiment of FIG. 17, parts similar to those of the embodiment of FIGS. 2–8 are designated by the same reference numerals followed by the suffix "A". The embodiment of FIG. 17 includes a valve actuator section 320 designed to work with a needle section 322.

The valve actuator section 320 includes as its principal parts s support plate 324, a valve actuator subassembly and sensors 336A and 336B. The valve actuator subassembly includes the valve actuator 61A and the motor assembly 340. The support plate 324 is vertically mounted to side posts and includes a substantially vertical flat portion having a horizontal forwardly extending socket 226 sized to receive and hold a needle subassembly 62A and an opening 328 to receive the drive shaft of the motor 340 from the rearward side of the support plate 324. The valve actuator 61A includes a flat rotatable disk 332 having two actuator pins 334A and 334B extending from the front surface of the rotatable disk 332 in spaced apart relation to each other so as to orbit about the center of rotation of the rotatable disk 332 in an oscillatory motion under the control of the motor 340. For this purpose the rotatable disk 332 is mounted to the drive shaft of the motor 340. To control the rotation of the disk 332, two Hall effect sensors 334A and 334B are mounted to the plate 324 along the periphery of the rotatable disk 332 to sense the disk and change its direction of rotation.

In operation, the valve actuator pins engage the cam follower pins 99A of the valve (FIG. 16) in the manner of the bifurcated member 61 of the embodiment of FIGS. 2–8 to open and close the valve of the sample containers in the refill station. The motor 340 rotates the disk 61A in one direction until one of the Hall effect sensors 336A and 336 senses the end position of a stroke to open or close the valve and then reverses direction until the other of the Hall effect sensors senses the end position for the other of the open or closed valve. The signals to the motor 340 are guided along the hollow guide 342.

The needle section operates in substantially the same manner as the needle drive of the embodiment of FIGS. 2–8 and for this purpose includes a needle subassembly 62A having the hollow needle 83A mounted to the support base 117A with end nipple 116A positioned to receive fluid to apply to the sample container. The hollow needle 83A ends in the hollow ball 103A having openings downwardly and lateral openings in the needle near it to supply liquid. The ball seals the cap of the sample bottle as the needle proceeds to the bottom of the container and moves upwardly in the manner of the embodiment of FIGS. 2–8 to fill the container.

In FIG. 18, there is shown a block diagram 120 of a program for operating the sampler comprising the general section 122 representing the off state, the sequence 124 representing the stand-by state and the sequence 126 representing the run state. During the off state, the decision program step 128 checks the on/off key and recirculates the off sequence if the key is off. If it is on, it sequences to the stand-by state 124.

In the stand-by state 124, if the decision step 130 on the on/off key indicates off, the program recirculates back to step 128. If the off key is not on, the program sequences to step 132 and tests it. If the program key is not on, the program sequences to step 138 for the set up key and if that is not on, it sequences to step 140 for the run key. If the run key is on, the program sequences to step 142 which is the sampling step in the run sequence 126. If the step of testing the program key 132 is positive, then the program sequences to step 134 of doing a program sequence. After that, it tests for the set up key step 138. If that decision is positive then it does a set up sequence as indicated by the step 136 and then sequences to testing the run key at step 140. If the run key is negative, the program recirculates back to the decision for the on/off key at step 130. If it is on, then the program sequences to the sampling sequence 142.

In FIG. 19, there is shown a block diagram of the program sequence 134 shown in FIG. 18. In the program sequence 134, the decision step for selecting the pacing 144 is first taken. If flow pacing is selected, the program proceeds to step 148 for entering the flow interval and from there to the decision step 150 for determining if there are to be duplicate samples.

If the time decision is selected at the step for selecting pacing 144, then the time interval is entered at step 146 and the program proceeds to the decision step 150 for determining if there are duplicate samples. If the answer to there being duplicate samples is yes, then the program for entering the numbers of the duplicates at step 152 is entered, after which the program proceeds to entering the number of samples at step 154. If duplicate samples are not to be entered, then the program proceeds immediately to the step 154 for entering the number of samples. After completing the program for entering the number of samples at 154, a sequence is performed to enter the start time at 156.

Figure 20:
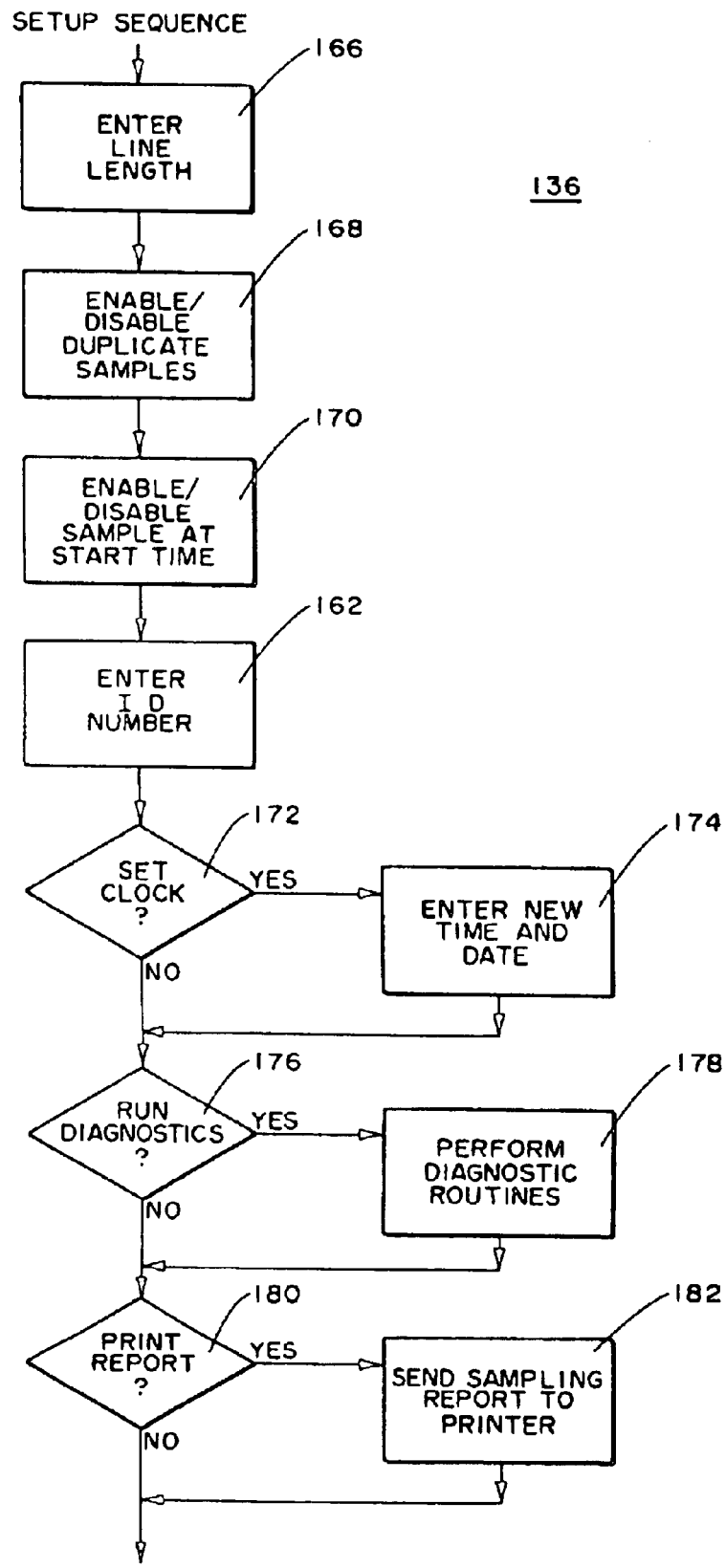
FIG. 20 is a block diagram of another portion of the program of FIG. 12.

In FIG. 20, there is shown the subsequence 136 (FIG. 18) for performing the set up sequence. As shown in this FIG. 20, the sequence starts with the step 166 of entering line length. It proceeds to the step 168 of enable/disable duplicate samples and from there to the step 170 of enable/disable sample at start time.

After the steps 166, 168 and 170 of entering beginning parameters, the I.D. number is entered at step 162. From there, the program proceeds to the steps 172, 176 and 180, which are decision steps for setting the clock and running diagnostics. A step of printing reports may be included but is not in the preferred embodiment. If the clock is to be set, then the subroutine for entering new time and date at 174 is entered into. If the step for running the diagnostic is to be entered into, then step 178 is entered into for performing diagnostic routines and if the step to print reports at 180 is to be entered into, then the subsequence for 182 for sending sampling reports to the printer is entered into. Otherwise, the steps proceed in the sequence 172, 176 and 180 as the operator defaults on those operations.

In FIG. 21, the subsequence 142 (FIG. 18) for sampling is shown, which subsequence proceeds through the substeps 200 for sample set up, to the substep for taking one sample at 202 and to the decision step 204 for determining if there are to be duplicate samples. If there are to be duplicate samples, then the decision step recirculates back to the sequence 202 for the next sample. If there are not to be duplicate samples, then the program proceeds to the subsequence for the number of samples at 206. If a programmed number of samples has been taken, it returns to the stand-by state shown at 208. Otherwise the sequence returns to 200.

In FIG. 22, there are shown the substeps for the sequence 200 (FIG. 21) for sample set up. In this sequence, the first step 212 is a decision step for determining if its past the start time. If it is not, then the program recirculates back to the beginning of the step. If it is past the start time, the decision step 212 proceeds to the decision step 214 for determining if its time or flow pacing. This decision step may also be entered from the decision step 206 (FIG. 21) as indicated at 210 (FIG. 22). The time or flow pacing step 214 chooses either to proceed to step 220 which is a decision step for determining if the sample is at the start and is the first sample. Otherwise, it proceeds through the flow sequence to the decision 218 to determine if the flow interval has expired.

At step 220, if the sample is the first sample and at the subsequence start, then it proceeds to step 224 for purging the sample line. If it is not, then it proceeds to the time interval expired step 222. If this step is no, then it recirculates to the beginning of the step and if it is yes, it proceeds to step 224 for purging the sample line. If the flow pacing decision is made at step 214, then it proceeds to the decision step determining if the flow is expired at 218. If it is not, it recirculates back through that step and if it is, it proceeds to the purged sample line step at 224.

In FIG. 23, there is shown the subsequence for the step 202 for taking one sample. In this sequence, the first substep at 226 is to move to the next bottle, the second substep at 228 is to open the valve and lower the needle assembly, the third substep at 230 is to start a pumping sample, the fourth substep at 232 is to raise the needle at the top of the bottle, the fifth substep at 234 is to pause, the sixth substep at 236 is to lower the needle, the seventh substep at 238 is to pause, the eighth substep at 240 is to raise the needle out of the bottle and the nineth substep at 242 is to move the needle to the top, close the valve and stop the pump.

In FIG. 24, there is shown the subsequence 206 for taking a number of samples (FIG. 21) including first, the decision step 244 for determining if the rack reset key has been pressed. If it has, then the program proceeds to the sequence 246 for returning the bottle rack to home and from there to the step 208 for returning to the stand-by state. If the answer is no at the decision step for determining if the rack reset key has been depressed, then the program proceeds to step 248 for deciding if the required number of samples has been taken. If it has, then the program proceeds to the return to stand-by state 208. If it hasn't, then it recirculates as shown at 210 to the subroutine 200 (FIG. 19) for setting up the next sample.

From the above description, it can be understood that the sample collector of this invention has several advantages, such as: (1) it can obtain samples automatically and repeatedly without human intervention; and (2) it collects samples without the escape of any substantial amounts of volatile material in the liquid. Although a preferred embodiment of the invention has been described with some particularity, many modifications and variations of the invention are possible within the light of the above teachings. Therefore, it is to be understood that, within the scope of the appended claims, the invention may be practiced other than as specifically described.

What is claimed is:

1. A method of sampling liquids comprising the steps of:
   drawing liquid from a heated fluid;
   cooling the liquid to a temperature lower than 84 degrees Fahrenheit;
   causing the liquid to flow through a needle into a container after it is cooled until the container overflows;
   removing the needle; and
   closing the container automatically as the needle is withdrawn.

2. The method of claim 1 in which the liquid is cooled within a housing having a cooled interior for a sufficient amount of time to reduce its temperature to less than 84 degrees Fahrenheit prior to moving the liquid into the container.

3. The method of claim 2 in which the liquid is moved through a long ballast tube within the housing, said ballast tube being sufficiently long to maintain the liquid in the housing until it is at a temperature lower than 84 degrees Fahrenheit.

4. A method according to claim 1 further including the step of causing the liquid to flow continuously as the needle is withdrawn through a valve opening.

5. The method of claim 1 in which a valve is open to atmosphere for less than ten minutes.

6. The method of claim 1 in which the step of causing the liquid to flow includes the substeps of automatically opening a valve with a narrow clearance between the needle and valve opening just before the needle enters the container to permit the needle to pass through it; causing the liquid to flow outwardly from the needle; causing the liquid to continue to flow as the needle is removed; and automatically closing the valve as soon as the needle clears the valve opening, whereby the liquid retains its volatile material during sampling.

7. A method in accordance with claim 1 in which the liquid is caused to flow from the needle laterally outwardly as the needle is withdrawn.

8. A method in accordance with claim 6 wherein the steps of automatically opening and closing the valve include the substep of rotating a rotatable member.

9. A method in accordance with claim 1 further including the step of sequentially bringing a plurality of containers into juxtaposition with at least one filling station for filling the container.

10. A method in accordance with claim 6 in which the substeps of opening the valve and closing the valve are synchronized with the steps of inserting a needle and withdrawing a needle so as to reduce the communication of the interior of the container with the atmosphere.

11. An apparatus for sampling liquids, comprising:
    means for cooling a liquid to below 40 degrees Fahrenheit;
    means for causing the liquid to flow through a needle into a container until the container overflows;
    means for removing the needle; and
    means for closing the container automatically as the needle is withdrawn.

12. The apparatus of claim 11 in which the means for cooling includes a housing having a cooled interior.

13. The apparatus of claim 12 in which the means for cooling further includes a long ballast tube within the housing, said ballast tube being sufficiently long to reduce the temperature of the liquid in the housing to a temperature lower than 84 degrees Fahrenheit.

14. An apparatus according to claim 11 further including means for causing the liquid to flow continuously as the needle is withdrawn.

15. The apparatus of claim 14 in which the means for causing the liquid to flow though the needle into a container includes:
    means for causing the liquid to flow through the needle to the bottom of the container;
    a valve with a narrow clearance between the needle and valve opening;
    means for automatically opening the valve as the needle enters the container;
    means for causing the liquid to flow outwardly from the needle and to overflow through the valve opening;
    means for pumping the liquid as the needle is removed, whereby the liquid continues to flow; and
    means for closing the valve as soon as the needle clears the valve opening, whereby the liquid retains its volatile material during sampling.

16. Apparatus in accordance with claim 15 further including means for causing the liquid to flow from the needle laterally outwardly as the needle is withdrawn.

17. Apparatus in accordance with claim 15 in which the valve includes a valve opening in a rotatable member, wherein the container is closed and opened automatically by rotating the rotatable member as the needle moves downwardly toward the container or upwardly away from the container.

18. A method of sampling liquid comprising the steps of:
    cooling the liquid:
    causing the liquid to flow through a needle into a container until the container overflows;
    removing the needle; and
    closing the container automatically as the needle is withdrawn.

19. The method of claim 18 in which the liquid is cooled within a housing having a cooled interior for a sufficient amount of time to reduce its temperature to less than 84 degrees Fahrenheit prior to moving the liquid into the container.

20. The method of claim 19 in which the liquid is moved through a long ballast tube within the housing, said ballast tube being sufficiently long to maintain the liquid in the housing until it is at a temperature lower than 84 degrees Fahrenheit.

21. A method according to claim 18 further including the step of causing the liquid to flow continuously as the needle is withdrawn through an opening.

22. The method of claim 18 in which a valve is open to atmosphere for less than ten minutes.

23. The method of claim 18 in which the step of causing the liquid to flow includes the substeps of automatically opening a valve with a narrow clearance between the needle and valve opening just before the needle enters the container to permit the needle to pass through it; causing liquid to flow outwardly from the needle; causing the liquid to continue to flow as the needle is removed; and closing the valve as soon as the needle clears the valve opening, whereby the liquid retains its volatile material during sampling.

24. A method in accordance with claim 18 in which the liquid is caused to flow from the needle laterally outwardly as the needle is withdrawn.

25. A method in accordance with claim 23 wherein the steps of opening and closing the valve include the substep of rotating a rotatable member.

26. A method in accordance with claim 25 further including the step of sequentially bringing a plurality of containers into juxtaposition with at least one filling station for filling the container.

27. A method in accordance with claim 23 in which the substeps of opening the valve and closing the valve are synchronized with the steps of inserting a needle and withdrawing a needle so as to reduce the communication of the interior of the container with the atmosphere.

28. An apparatus for sampling liquids, comprising:
   means for drawing liquid;
   means for cooling the liquid;
   means for causing the liquid to flow through a needle into a container until the container overflows;
   means for removing the needle; and
   means for closing the container automatically as the needle is withdrawn.

29. The apparatus of claim 28 in which the means for cooling includes a housing having a cooled interior.

30. The apparatus of claim 29 in which the means for cooling further includes a long ballast tube within the housing, said ballast tube being sufficiently long to reduce the temperature of the liquid in the housing to a temperature lower than 84 degrees Fahrenheit.

31. An apparatus according to claim 28 further including means for causing the liquid to flow continuously as the needle is withdrawn.

32. The apparatus of claim 28 in which the means for causing the liquid to flow through the needle into a container includes:
   means for causing the liquid to flow through the needle to the bottom of the container;
   a valve with a narrow clearance between the needle and valve opening;
   means for automatically opening the valve as the needle enters the container;
   means for causing the liquid to flow outwardly from the needle and to overflow through the valve opening;
   means for pumping the liquid as the needle is removed, whereby liquid continues to flow; and
   means for closing the valve as soon as the needle clears the valve opening, whereby the liquid retains its volatile material during sampling.

33. Apparatus in accordance with claim 28 further including means for causing the liquid to flow from the needle laterally outwardly as the needle is withdrawn.

34. Apparatus in accordance with claim 28 in which a valve includes a valve opening in a rotatable member, wherein the container is closed and opened automatically by rotating the rotatable member as the needle moves downwardly toward the container or upwardly away from the container.

35. Apparatus in accordance with claim 28 further including means for sequentially bringing a plurality of containers and stations into juxtaposition with each other for filling of the containers.

36. A method of sampling liquid comprising the steps of:
   cooling the liquid:
   inserting a hollow needle into a container having a cap with a valve member and an opening in the valve member sized to narrowly receive the hollow needle;
   causing the liquids to flow through the needle until the container overflows;
   removing the needle; and
   closing the container automatically as the needle is withdrawn.

37. The method of claim 36 in which the liquid is cooled within a housing having a cooled interior for a sufficient amount of time to reduce its temperature to less than 84 degrees Fahrenheit prior to moving the liquid into the container.

38. The method of claim 36 in which the liquid is moved through a long ballast tube within the housing, said ballast tube being sufficiently long to maintain the liquid in the housing until it is at a temperature lower than 84 degrees Fahrenheit.

39. A method according to claim 36 in which the hollow needle is extended through the opening in the valve member while the valve member opening is perpendicular to a longitudinal axis of the valve member and adapted to fit a container opening and turning the valve member to another position to close the container opening.

40. A method in accordance with claim 36 further including the step of automatically opening and closing the valve member.

41. The method of claim 40 in which the step of automatically opening and closing the valve member comprises the step of engaging a cam follower connected to the valve member with a cam.

42. An apparatus for sampling liquids, comprising:
   means for cooling a liquid to below 40 degrees Fahrenheit;
   means for causing the liquid to flow through a hollow needle into a container until the container overflows to a level on the top of at least a portion of a container cap;
   means for removing the needle; and
   means for closing the container automatically as the needle is withdrawn;
   said container cap including an upper portion; said upper portion having a valve member and an opening in the valve member sized to narrowly receive the hollow needle in the valve member.

43. The apparatus of claim 42 in which the means for cooling includes a housing having a cooled interior.

44. The apparatus of claim 43 in which the means for cooling further includes a long ballast tube within the housing, said ballast tube being sufficiently long to reduce the temperature of the liquid in the housing to a temperature lower than 84 degrees Fahrenheit.

45. Apparatus according to claim 42 in which the valve member extends through the opening in the valve member while the valve member opening is perpendicular to a longitudinal axis of the valve member and is adapted to be aligned in one position with a container opening and in another position to close the container opening.

46. Apparatus in accordance with claim 42 in which the valve member includes a cam follower on one end adapted to engage with a cam for opening and closing the valve opening.

47. Apparatus in accordance with claim 42 further including a closure portion adapted to engage an opening of the container.

48. Apparatus according to claim 46 in which the valve member includes a valve member handle and the length of the valve member handle is no smaller than 0.240 inch nor greater than 0.750 inch.

49. Apparatus according to claim 48 in which the length of the valve member handle is no smaller than 0.125 nor greater than 1.6 inches.

50. Apparatus according to claim 49 in which the outer diameter of the valve member handle is no smaller than 0.700 inch nor greater than 0.950 inch.

51. Apparatus according to claim 45 in which a valve passageway has a diameter no narrower than 0.150 nor greater 0.500 inch.

52. A method of filling a container with liquid through a valve having a valve opening comprising the steps of:

placing a cap having said valve and a valve actuator on the top of the container;

actuating the valve actuator to open a conduit between the top and bottom of the cap to the bottom through said valve opening, whereby a needle may be inserted through the valve opening and into the container to fill the container while allowing liquid to flow up into the top of the cap; and actuating the valve to close the opening after withdrawing the needle through the conduit when the container is filled, whereby the valve may be closed while liquid is above it;

said step of actuating the valve including the step of automatically actuating the valve actuator in synchronization with the needle.

53. A method in accordance with claim 52 further including the step of closing an opening in the top of the cap before the needle is inserted through the valve opening.

54. A method in accordance with claim 53 in which the step of closing an opening includes the step of moving a fluid socket of a needle assembly into an upwardly extending funnel shaped cavity of the cap, wherein the funnel is sized and shaped to receive the fluid socket of the needle assembly so the socket seals the cavity during filling.

55. A method in accordance with claim 53 in which the step of closing an opening includes the step of moving a fluid socket over the cap, wherein the cap is sized to fit within the socket.

56. A method according to claim 52 in which the step of inserting the needle includes the steps of:

inserting the needle through an upwardly extending funnel shaped cavity adapted to receive overflowing liquid;

inserting the needle through a valve member located below the cavity, wherein said valve member has an opening to narrowly receive a hollow needle wherein the valve may be closed while permitting liquid to be maintained in the cavity above the valve during filling of the container, thus preventing the container from being exposed to atmosphere through the valve;

inserting the needle through the narrow opening, wherein all valves between the bottom of the cap and the cavity are arranged to remain open until closed by an external force; and filling the container as the needle is withdrawn until the funnel is full.

57. A method in accordance with claim 52 in which the valve opening is perpendicular to the longitudinal axis of the valve member, wherein the step of actuating the valve includes the step of aligning the opening in one position with the container to open the container, and aligning the opening in a second position to close the container.

58. A method in accordance with claim 52 in which the step of actuating the valve actuator includes the step of gripping the valve actuating member with a valve grip when the container is moved to a filling station, wherein a valve grip rotates in response to movement of a cam follower engaged by a cam shaft to either open or close the valve.

59. A method in accordance with claim 52 in which the step of actuating the valve actuator includes the step of turning a horizontally-positioned valve actuator to permit automatic opening and closing of the valve, wherein said valve actuator has a height no smaller than 0.250 inch nor greater than 0.750 inch.

60. A method in accordance with claim 52 in which the step of actuating the valve actuator includes the steps of turning a horizontally-positioned valve actuator to permit automatic opening and closing of the valve; said valve actuator having a length no smaller than 0.250 inch nor greater than 0.750 inch.

* * * * *